(12) United States Patent
Gurtner et al.

(10) Patent No.: US 9,228,027 B2
(45) Date of Patent: *Jan. 5, 2016

(54) THREADS OF HYALURONIC ACID AND/OR DERIVATIVES THEREOF, METHODS OF MAKING THEREOF AND USES THEREOF

(75) Inventors: Geoffrey C. Gurtner, Stanford, CA (US); Kenneth N. Horne, San Francisco, CA (US); Jayakumar Rajadas, Cupertino, CA (US)

(73) Assignee: Allergan Holdings France S.A.S., Courbevoie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/060,919

(22) PCT Filed: Sep. 2, 2009

(86) PCT No.: PCT/US2009/055704
§ 371 (c)(1),
(2), (4) Date: May 19, 2011

(87) PCT Pub. No.: WO2010/028025
PCT Pub. Date: Mar. 11, 2010

(65) Prior Publication Data
US 2011/0263724 A1    Oct. 27, 2011

Related U.S. Application Data

(60) Provisional application No. 61/190,866, filed on Sep. 2, 2008.

(51) Int. Cl.
| | | |
|---|---|---|
| *A61K 31/728* | (2006.01) | |
| *A61K 9/70* | (2006.01) | |
| *C08B 37/08* | (2006.01) | |
| *A61L 15/28* | (2006.01) | |
| *A61L 17/06* | (2006.01) | |
| *A61L 27/20* | (2006.01) | |

(Continued)

(52) U.S. Cl.
CPC ............. *C08B 37/0072* (2013.01); *A61L 15/28* (2013.01); *A61L 17/06* (2013.01); *A61L 27/20* (2013.01); *A61L 31/042* (2013.01); *C08L 5/08* (2013.01); *Y10T 428/2929* (2015.01)

(58) Field of Classification Search
None
See application file for complete search history.

(56) References Cited

U.S. PATENT DOCUMENTS 2,128,827 A    8/1938 Killian
3,548,056 A    12/1970 Eigen et al.

(Continued)

FOREIGN PATENT DOCUMENTS

AU    2004261752    2/2005
AU    2005219595    9/2005

(Continued)

OTHER PUBLICATIONS

"Thread augmentation for facial rhytides" by Conley et al., Ann. Plast. Surg. 3, 118-26 (1979) (PubMed Abstract No. 396849).*

(Continued)

*Primary Examiner* — Theodore R West
(74) *Attorney, Agent, or Firm* — Linda Allyson Nassif; Barbara C. Potts

(57) ABSTRACT

The present invention provides threads of hyaluronic acid, and/or derivatives thereof, methods of making thereof and uses thereof, for example, in aesthetic applications (e.g., dermal fillers), surgery (sutures), drug delivery, etc.

17 Claims, 12 Drawing Sheets

(51) Int. Cl.
*A61L 31/04* (2006.01)
*C08L 5/08* (2006.01)

(56) References Cited

U.S. PATENT DOCUMENTS

| | | |
|---|---|---|
| 3,763,009 A | 10/1973 | Suzuki |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,500,676 A | 2/1985 | Balazs et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs |
| 4,642,117 A | 2/1987 | Nguyen et al. |
| 4,713,448 A | 12/1987 | Balazs |
| 4,716,154 A | 12/1987 | Maelson et al. |
| 4,772,419 A | 9/1988 | Malson et al. |
| 4,803,075 A | 2/1989 | Wallace et al. |
| 4,851,521 A | 7/1989 | della Valle et al. |
| 4,886,787 A | 12/1989 | De Belder et al. |
| 4,896,787 A | 1/1990 | Delamour et al. |
| 4,902,508 A | 2/1990 | Badylak et al. |
| 4,956,178 A | 9/1990 | Badylak et al. |
| 4,957,744 A | 9/1990 | della Valle et al. |
| 4,963,666 A | 10/1990 | Malson |
| 4,965,353 A | 10/1990 | della Valle et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner et al. |
| 5,211,644 A | 5/1993 | VanBeek et al. |
| 5,246,698 A | 9/1993 | Leshchiner et al. |
| 5,281,422 A | 1/1994 | Badylak et al. |
| 5,314,874 A | 5/1994 | Miyata et al. |
| 5,328,955 A | 7/1994 | Rhee et al. |
| 5,336,767 A | 8/1994 | della Valle et al. |
| 5,352,463 A | 10/1994 | Badylak et al. |
| 5,356,883 A | 10/1994 | Kuo et al. |
| 5,372,821 A | 12/1994 | Badylak et al. |
| 5,399,351 A | 3/1995 | Leshchiner et al. |
| 5,428,024 A | 6/1995 | Chu et al. |
| 5,445,833 A | 8/1995 | Badylak et al. |
| 5,516,533 A | 5/1996 | Badylak et al. |
| 5,520,916 A | 5/1996 | Dorigatti et al. |
| 5,527,856 A | 6/1996 | Rhee et al. |
| 5,531,716 A | 7/1996 | Luzio et al. |
| 5,550,187 A | 8/1996 | Rhee et al. |
| 5,565,519 A | 10/1996 | Rhee et al. |
| 5,571,503 A | 11/1996 | Mausner |
| 5,573,784 A | 11/1996 | Badylak et al. |
| 5,614,587 A | 3/1997 | Rhee et al. |
| 5,616,568 A | 4/1997 | Pouyani et al. |
| 5,616,611 A | 4/1997 | Yamamoto |
| 5,616,689 A | 4/1997 | Shenoy et al. |
| 5,622,707 A | 4/1997 | Dorigatti et al. |
| 5,633,001 A | 5/1997 | Agerup |
| 5,641,518 A | 6/1997 | Badylak et al. |
| 5,643,464 A | 7/1997 | Rhee et al. |
| 5,644,049 A | 7/1997 | Giusti et al. |
| 5,645,860 A | 7/1997 | Knapp, Jr. et al. |
| 5,668,288 A | 9/1997 | Storey et al. |
| 5,676,964 A | 10/1997 | della Valle |
| 5,695,998 A | 12/1997 | Badylak et al. |
| 5,711,969 A | 1/1998 | Patel et al. |
| 5,718,012 A | 2/1998 | Cavallaro |
| 5,730,933 A | 3/1998 | Peterson |
| 5,733,868 A | 3/1998 | Peterson et al. |
| 5,735,863 A | 4/1998 | Della Valle et al. |
| 5,753,267 A | 5/1998 | Badylak et al. |
| 5,755,791 A | 5/1998 | Whitson et al. |
| 5,762,966 A | 6/1998 | Knapp, Jr. et al. |
| 5,782,913 A | 7/1998 | Schindler et al. |
| 5,788,625 A | 8/1998 | Plouhar et al. |
| 5,823,671 A | 10/1998 | Mitchell et al. |
| 5,824,333 A | 10/1998 | Scopelianos et al. |
| 5,824,335 A | 10/1998 | Dorigatti et al. |
| 5,827,529 A | 10/1998 | Ono et al. |
| 5,827,937 A | 10/1998 | Ang |
| 5,843,907 A | 12/1998 | Sakai |
| 5,866,414 A | 2/1999 | Badylak et al. |
| 5,879,359 A | 3/1999 | Dorigatti et al. |
| 5,885,619 A | 3/1999 | Patel et al. |
| 5,886,042 A | 3/1999 | Yu et al. |
| 5,922,028 A | 7/1999 | Plouhar et al. |
| 5,935,164 A | 8/1999 | Iversen |
| 5,941,910 A | 8/1999 | Schindler et al. |
| 5,972,326 A | 10/1999 | Galin et al. |
| 5,980,930 A * | 11/1999 | Fenton et al. ................ 424/443 |
| 6,013,679 A | 1/2000 | Kuo et al. |
| 6,056,777 A | 5/2000 | McDowell |
| 6,066,325 A | 5/2000 | Wallace et al. |
| 6,086,578 A | 7/2000 | Adamyan et al. |
| 6,139,520 A | 10/2000 | McCrory et al. |
| 6,140,257 A | 10/2000 | Kershaw et al. |
| 6,224,857 B1 | 5/2001 | Romeo et al. |
| 6,312,421 B1 | 11/2001 | Boock |
| 6,335,035 B1 | 1/2002 | Drizen et al. |
| 6,339,074 B1 | 1/2002 | Cialdi et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,387,413 B1 | 5/2002 | Miyata et al. |
| 6,418,934 B1 | 7/2002 | Chin |
| 6,432,710 B1 | 8/2002 | Boss et al. |
| 6,521,223 B1 | 2/2003 | Calias et al. |
| 6,544,503 B1 | 4/2003 | Vanderhoff et al. |
| 6,579,978 B1 | 6/2003 | Renier et al. |
| 6,602,859 B2 | 8/2003 | Miyamoto et al. |
| 6,627,620 B1 | 9/2003 | Nielsen |
| 6,630,486 B1 | 10/2003 | Royer |
| 6,632,802 B2 | 10/2003 | Bellini et al. |
| 6,638,538 B1 | 10/2003 | Hashimoto et al. |
| 5,880,107 A1 | 11/2003 | Khan |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,833,488 B2 | 12/2004 | Bucevschi et al. |
| 6,852,255 B2 | 2/2005 | Yang et al. |
| 6,872,819 B1 | 3/2005 | Pavesio et al. |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,014,860 B1 | 3/2006 | Kawata et al. |
| 7,087,745 B1 | 8/2006 | Pallado et al. |
| 7,119,062 B1 | 10/2006 | Alvis et al. |
| 7,125,860 B1 | 10/2006 | Renier et al. |
| 7,166,570 B2 | 1/2007 | Hunter et al. |
| 7,192,984 B2 | 3/2007 | Berg et al. |
| 7,196,180 B2 | 3/2007 | Aeschlimann |
| 7,214,765 B2 | 5/2007 | Ringeisen et al. |
| 7,244,270 B2 | 7/2007 | Lesh |
| 7,314,636 B2 | 1/2008 | Caseres et al. |
| 7,323,425 B2 | 1/2008 | Chu et al. |
| 7,491,709 B2 | 2/2009 | Carey |
| 7,504,386 B2 | 3/2009 | Pressato et al. |
| 7,559,952 B2 | 7/2009 | Pinchuk |
| 7,637,900 B2 | 12/2009 | Burgess et al. |
| 7,666,339 B2 | 2/2010 | Chaouk et al. |
| 7,741,476 B2 | 6/2010 | Lebreton |
| 7,807,656 B2 | 10/2010 | Reinmuller |
| 7,850,985 B2 | 12/2010 | Patel et al. |
| 7,902,171 B2 | 3/2011 | Reinmuller et al. |
| 7,910,690 B2 | 3/2011 | Ringeisen et al. |

(56) References Cited

U.S. PATENT DOCUMENTS

| | | |
|---|---|---|
| 7,998,202 B2 | 8/2011 | Lesh |
| 8,021,323 B2 | 9/2011 | Arora et al. |
| 8,038,665 B2 | 10/2011 | Burgess et al. |
| 8,052,990 B2 | 11/2011 | Hermitte et al. |
| 8,124,120 B2 | 2/2012 | Sadozai |
| 8,147,811 B1 | 4/2012 | Dalle Carbonare et al. |
| 8,240,314 B2 | 8/2012 | Fletcher |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Stroumpoulis et al. |
| 8,394,783 B2 | 3/2013 | Stroumpoulis et al. |
| 8,394,784 B2 | 3/2013 | Stroumpoulis et al. |
| 8,450,475 B2 | 5/2013 | Lebreton |
| 8,455,465 B2 | 6/2013 | Molliard |
| 8,513,216 B2 | 8/2013 | Stroumpoulis et al. |
| 8,524,213 B2 | 9/2013 | Leshchiner et al. |
| 8,563,532 B2 | 10/2013 | Lebreton |
| 8,575,129 B2 | 11/2013 | Bellini |
| 8,586,562 B2 | 11/2013 | Lebreton |
| 8,901,202 B2 | 12/2014 | Pastorello et al. |
| 2001/0008937 A1 | 7/2001 | Callegaro et al. |
| 2002/0026039 A1 | 2/2002 | Bellini et al. |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0068297 A1 | 4/2003 | Jain |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0006319 A1 | 1/2004 | Lina et al. |
| 2004/0032056 A1 | 2/2004 | Vang et al. |
| 2004/0101959 A1 | 5/2004 | Marko et al. |
| 2004/0127698 A1* | 7/2004 | Tsai et al. ............... 536/53 |
| 2004/0127699 A1 | 7/2004 | Zhao et al. |
| 2004/0192643 A1 | 9/2004 | Pressato et al. |
| 2004/0199241 A1 | 10/2004 | Gravett et al. |
| 2004/0265389 A1 | 12/2004 | Yui et al. |
| 2005/0033362 A1 | 2/2005 | Grafton |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0187185 A1* | 8/2005 | Reinmuller ............... 514/54 |
| 2005/0226936 A1 | 10/2005 | Agerup |
| 2005/0271729 A1 | 12/2005 | Wang |
| 2005/0281880 A1 | 12/2005 | Wang |
| 2005/0287180 A1 | 12/2005 | Chen |
| 2006/0040894 A1 | 2/2006 | Hunter et al. |
| 2006/0041320 A1 | 2/2006 | Matsuda |
| 2006/0073207 A1 | 4/2006 | Masters et al. |
| 2006/0095137 A1 | 5/2006 | Chung et al. |
| 2006/0105022 A1* | 5/2006 | Yokokawa et al. ......... 424/439 |
| 2006/0122147 A1 | 6/2006 | Wohlrab |
| 2006/0136070 A1 | 6/2006 | Pinchuk et al. |
| 2006/0141049 A1 | 6/2006 | Lyons et al. |
| 2006/0147483 A1 | 7/2006 | Chaouk et al. |
| 2006/0148755 A1 | 7/2006 | Bailleul |
| 2006/0166928 A1 | 7/2006 | Moon et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0264698 A1 | 11/2006 | Kondonis et al. |
| 2006/0286769 A1 | 12/2006 | Tsuchiya et al. |
| 2007/0026070 A1* | 2/2007 | Vonwiller et al. ............ 424/486 |
| 2007/0032805 A1 | 2/2007 | Therin et al. |
| 2007/0066816 A1 | 3/2007 | Tsai et al. |
| 2007/0077292 A1 | 4/2007 | Pinsky |
| 2007/0196426 A1 | 8/2007 | Hermitte et al. |
| 2007/0197754 A1 | 8/2007 | White et al. |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0097605 A1 | 4/2008 | Pastorello et al. |
| 2008/0118563 A1 | 5/2008 | Muzzarelli et al. |
| 2008/0188416 A1 | 8/2008 | Bernstein |
| 2008/0193538 A1 | 8/2008 | Kitazono et al. |
| 2008/0200430 A1 | 8/2008 | Biterman et al. |
| 2008/0207560 A1 | 8/2008 | Harada et al. |
| 2008/0207794 A1 | 8/2008 | Wright et al. |
| 2008/0241252 A1 | 10/2008 | Lyons |
| 2008/0248079 A1 | 10/2008 | Dempsey et al. |
| 2008/0268051 A1 | 10/2008 | Lyons |
| 2008/0274946 A1 | 11/2008 | Giampapa |
| 2008/0279806 A1 | 11/2008 | Cho |
| 2008/0293637 A1 | 11/2008 | Schroeder et al. |
| 2009/0017091 A1 | 1/2009 | Daniloff et al. |
| 2009/0018102 A1 | 1/2009 | Moutet |
| 2009/0022808 A1 | 1/2009 | Championn |
| 2009/0028817 A1 | 1/2009 | Niklason et al. |
| 2009/0030367 A1 | 1/2009 | Arora et al. |
| 2009/0036403 A1 | 2/2009 | Stroumpoulis et al. |
| 2009/0042834 A1 | 2/2009 | Karageozian et al. |
| 2009/0043268 A1 | 2/2009 | Eddy et al. |
| 2009/0093755 A1 | 4/2009 | Schroeder |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel |
| 2009/0148527 A1 | 6/2009 | Robinson |
| 2009/0155314 A1 | 6/2009 | Tezel et al. |
| 2009/0155362 A1 | 6/2009 | Longin |
| 2009/0169615 A1 | 7/2009 | Pinsky |
| 2009/0204101 A1 | 8/2009 | Wortzman et al. |
| 2009/0209456 A1 | 8/2009 | Sweis |
| 2009/0263447 A1 | 10/2009 | Asius et al. |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028435 A1 | 2/2010 | Gavard |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0221684 A1 | 9/2010 | Asius et al. |
| 2010/0226988 A1 | 9/2010 | Lebreton |
| 2010/0255068 A1 | 10/2010 | Stroumpoulis et al. |
| 2010/0303873 A1 | 12/2010 | Piron et al. |
| 2010/0310631 A1 | 12/2010 | Domard et al. |
| 2010/0316683 A1 | 12/2010 | Piron et al. |
| 2011/0034684 A1 | 2/2011 | Yokokawa et al. |
| 2011/0077737 A1 | 3/2011 | Stroumpoulis et al. |
| 2011/0118206 A1 | 5/2011 | Lebreton |
| 2011/0171286 A1 | 7/2011 | Cecile et al. |
| 2011/0171311 A1 | 7/2011 | Gousse et al. |
| 2011/0172180 A1 | 7/2011 | Gousse et al. |
| 2011/0224164 A1 | 9/2011 | Lebreton |
| 2011/0229574 A1 | 9/2011 | Guillen et al. |
| 2011/0263724 A1 | 10/2011 | Gurtner et al. |
| 2012/0010146 A1 | 1/2012 | Han et al. |
| 2012/0034462 A1 | 2/2012 | Stroumpoulis et al. |
| 2012/0071437 A1 | 3/2012 | Stroumpoulis et al. |
| 2012/0095206 A1 | 4/2012 | Chen |
| 2012/0100217 A1 | 4/2012 | Green |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189708 A1 | 7/2012 | Van Epps et al. |
| 2012/0190644 A1 | 7/2012 | D'este |
| 2012/0208890 A1 | 8/2012 | Gousse et al. |

(56) References Cited

U.S. PATENT DOCUMENTS

| | | |
|---|---|---|
| 2012/0225842 A1 | 9/2012 | Cecile et al. |
| 2012/0232030 A1 | 9/2012 | Gousse et al. |
| 2013/0018415 A1 | 1/2013 | Brown et al. |
| 2013/0023658 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0122068 A1 | 5/2013 | Fermanian et al. |
| 2013/0123210 A1 | 5/2013 | Liu |
| 2013/0131011 A1 | 5/2013 | Lebreton |
| 2013/0136780 A1 | 5/2013 | Tezel et al. |
| 2013/0203696 A1 | 8/2013 | Liu |
| 2013/0209532 A1 | 8/2013 | Stroumpoulis et al. |
| 2013/0210760 A1 | 8/2013 | Liu |
| 2013/0226235 A1 | 8/2013 | Fermanian et al. |
| 2013/0237615 A1 | 9/2013 | Meunier |
| 2013/0244943 A1 | 9/2013 | Yu et al. |
| 2013/0244970 A1 | 9/2013 | Lebreton |
| 2013/0274222 A1 | 10/2013 | Home |
| 2014/0011980 A1 | 1/2014 | Chitre et al. |
| 2014/0011990 A1 | 1/2014 | Lebreton |
| 2014/0228971 A1 | 8/2014 | Kim |

FOREIGN PATENT DOCUMENTS

| | | | |
|---|---|---|---|
| AU | 2009288118 A1 | 3/2010 | |
| AU | 2012318283 A | 5/2013 | |
| CA | 949965 | 6/1974 | |
| CA | 2264085 C | 10/2006 | |
| CA | 2735173 A1 | 3/2010 | |
| CA | 2791050 A1 | 9/2011 | |
| CA | 2815141 A1 | 4/2012 | |
| CN | 104144714 A | 11/2014 | |
| DE | 2912043 A1 | 1/1980 | |
| EP | 0273823 | 7/1988 | |
| EP | 0193510 B1 | 11/1988 | |
| EP | 341745 A1 * | 11/1989 | ........... A61K 31/725 |
| EP | 341745 A1 | 11/1989 | |
| EP | 0416250 | 3/1991 | |
| EP | 0416846 | 3/1991 | |
| EP | 341745 B1 | 12/1994 | |
| EP | 1 217 008 | 6/2002 | |
| EP | 1247522 | 10/2002 | |
| EP | 1419792 | 4/2003 | |
| EP | 1398131 | 3/2004 | |
| EP | 1532991 | 5/2005 | |
| EP | 1 217 008 | 3/2006 | |
| EP | 1 640 026 | 3/2006 | |
| EP | 1712228 A2 | 10/2006 | |
| EP | 1726299 | 11/2006 | |
| EP | 1 614 696 | 9/2007 | |
| EP | 2236523 | 10/2010 | |
| EP | 2324064 A4 | 7/2013 | |
| EP | 2629809 A1 | 8/2013 | |
| EP | 2766056 A1 | 8/2014 | |
| FR | 2733427 A1 | 10/1990 | |
| FR | 2733427 | 10/1996 | |
| FR | 2920000 | 2/2009 | |
| FR | 2924615 | 6/2009 | |
| JP | 55-153711 | 11/1980 | |
| JP | 2002080501 | 3/2002 | |
| JP | 2006-522851 | 10/2006 | |
| JP | 2006-522851 A | 10/2006 | |
| JP | 2007063177 | 3/2007 | |
| JP | 2007-520612 | 7/2007 | |
| JP | 2007-520612 A | 7/2007 | |
| JP | 2007-262595 | 10/2007 | |
| JP | 2007-262595 A | 10/2007 | |
| JP | 2012501391 A | 1/2012 | |
| JP | 2014533992 A1 | 12/2014 | |
| KR | 10-2008-0062092 | 7/2008 | |
| WO | 8600079 | 1/1986 | |
| WO | 8600912 | 2/1986 | |
| WO | 9200105 | 1/1992 | |
| WO | WO 92/13579 | 8/1992 | |
| WO | WO9213579 A1 | 8/1992 | |
| WO | 9220349 | 11/1992 | |
| WO | 9401468 | 1/1994 | |
| WO | 9402517 | 2/1994 | |
| WO | WO9524497 A1 | 9/1995 | |
| WO | 9633751 | 1/1996 | |
| WO | WO9637519 A1 | 11/1996 | |
| WO | 9704012 | 2/1997 | |
| WO | 9737613 A1 | 10/1997 | |
| WO | WO9808876 A1 | 3/1998 | |
| WO | 9835639 | 8/1998 | |
| WO | 9835640 | 8/1998 | |
| WO | WO9956799 A1 | 11/1999 | |
| WO | 0001428 | 1/2000 | |
| WO | WO 01/00190 | 1/2001 | |
| WO | 0179342 | 10/2001 | |
| WO | 0205753 | 1/2002 | |
| WO | 0206350 | 1/2002 | |
| WO | 0209792 | 2/2002 | |
| WO | 0217713 | 3/2002 | |
| WO | WO02/17979 | 3/2002 | ............ A61L 15/00 |
| WO | WO0217979 A1 | 3/2002 | |
| WO | 03007782 | 1/2003 | |
| WO | 2004020473 | 3/2004 | |
| WO | WO 2004/022603 | 3/2004 | |
| WO | WO 2004022603 | 3/2004 | |
| WO | WO2004022603 A1 | 3/2004 | |
| WO | WO 2004022603 A1 * | 3/2004 | |
| WO | 2004073759 | 9/2004 | |
| WO | 2004092222 A2 | 10/2004 | |
| WO | 2004092223 | 10/2004 | |
| WO | WO 2005/012364 | 2/2005 | |
| WO | 2005040224 | 5/2005 | |
| WO | 2005067944 | 7/2005 | |
| WO | 2005074913 | 8/2005 | |
| WO | WO 2005/085329 | 9/2005 | |
| WO | 2005112888 | 12/2005 | |
| WO | 2006023645 | 3/2006 | |
| WO | 2006067608 | 6/2006 | |
| WO | 2007018124 | 2/2007 | |
| WO | 2007070617 | 6/2007 | |
| WO | 2007077399 | 7/2007 | |
| WO | WO 2007/077399 | 7/2007 | |
| WO | 2007128923 | 11/2007 | |
| WO | 2007136738 | 11/2007 | |
| WO | 2008034176 | 3/2008 | |
| WO | WO 2008/056069 | 5/2008 | |
| WO | 2008068297 | 6/2008 | |
| WO | 2008072230 | 6/2008 | |
| WO | 2008072230 A1 | 6/2008 | |
| WO | 2008077172 | 7/2008 | |
| WO | 2008098019 | 8/2008 | |
| WO | 2008139122 | 11/2008 | |
| WO | 2008148967 | 12/2008 | |
| WO | 2008157608 | 12/2008 | |
| WO | WO 2008/157280 | 12/2008 | |
| WO | 2009024719 | 2/2009 | |
| WO | 2009026158 | 2/2009 | |
| WO | 2009028764 | 3/2009 | |
| WO | 2009034559 | 3/2009 | |
| WO | 2009073437 | 6/2009 | |
| WO | 2010003797 | 1/2010 | |
| WO | 2010027471 | 3/2010 | |
| WO | 2010029344 | 3/2010 | |
| WO | WO 2010/028025 | 3/2010 | |
| WO | 2010038771 | 4/2010 | |
| WO | 2010051641 | 5/2010 | |
| WO | 2010052430 | 5/2010 | |
| WO | 2010053918 | 5/2010 | |
| WO | WO 2010/052430 | 5/2010 | |
| WO | 2010061005 | 6/2010 | |
| WO | 2010061005 A1 | 6/2010 | |
| WO | 2010015900 | 2/2011 | |
| WO | WO 2011/109129 | 9/2011 | |

(56) References Cited

FOREIGN PATENT DOCUMENTS

| WO | WO 2011/109130 | 9/2011 |
|---|---|---|
| WO | WO 2012/054301 | 4/2012 |
| WO | WO 2012/054311 | 4/2012 |
| WO | 2012/077055 | 6/2012 |
| WO | WO2012089179 A1 | 7/2012 |
| WO | PCT/US2012/059618 | 10/2012 |
| WO | WO 2012/174464 | 12/2012 |
| WO | WO2013055832 A1 | 4/2013 |

OTHER PUBLICATIONS

International Search Report and Written Opinion from PCT/US2011/056182 dated Dec. 27, 2011, 15 pages.
International Search Report and Written Opinion from PCT/US2011/056216 dated Dec. 14, 2011, 10 pages.
U.S. Appl. No. 13/581,902, filed Jan. 26, 2011, Chee et al.
U.S. Appl. No. 13/649,051, filed Oct. 10, 2012, Fermanian et al.
International Search Report for PCT/US2012/059618 dated Dec. 11, 2012.
Supplementary European Search Report for EP 09812153.6 dated May 31, 2013.
Extended European Search Report dated May 22, 2013 for EP09812153.6.
International Search Report for PCT/US2011/22636, dated Jun. 16, 2011.
Haaf U, Breuninger H., "Resorbable Suture Material in the Human Skin: Tissue Reaction and Modified Suture Technic," Hautarzt, 39(1):23-7 (1988) (Abstract only).
Holzheimer, "Adverse Events of Sutures: Possible Interactions of Biomaterials?," European Journal of Medical Research, 10: 521-526 (2006).
Semchyshyn, N.L., "Dermatologic Surgical Complications," Medscape Reference, Drugs, Diseases & Procedures, 1-20 (2012).
Belda, Jose I., et al., "Hyaluronic acid combined with mannitol to improve protection against free-radical endothelial damage: Experimental Model," J.Cataract Refract Surg 2005; 31:1213-1218.
Goldberg "Breakthroughs in US dermal fillers for facial soft-tissue augmentation." J Cosmet Laser Ther. 11(4):240-247 (2009).
Aesthetic Buyers Guide, "Juvéderm Raises Standards" Jan./Feb. 2007 (5 pp.), www.miinews.com.
Adams, "An Analysis of Clinical Studies of the Uses of Crosslinked Hyaluronan, Hylan, in the Treatment of Osteoarthritis", J. Rheumatol Suppl., Aug. 1993; 39:16-8.
Albano, Emanuele, et al., "Hydroxyethyl Radicals in Ethanol Hepatotoxicity," Frontiers in Bioscience 4:533-540 (1999).
Allemann et al., "Hyaluronic acid gel (JUVEDERM) preparations in the treatment of facial wrinkles and folds", 2008, Clinical Interventions in Aging, vol. 3, No. 4, pp. 629-634.
Antunes, Alberto A., et al., "Efficacy of Intrarectal Lidocaine Hydrochloride Gel for Pain control in Patients Undergoing Transrectal Prostate Biopsy", International Braz J Urol, vol. 30(5): 380-383, Sep.-Oct. 2004.
Atanassoff, Peter G., et al., "The Effect of Intradermal Administration of Lidocaine and Morphine on the Response to Thermal Stimulation", Anesth Analg 1997; 84:1340-3.
Baumann et al. "JUVEDERM vs. ZYPLAST Nasolabial Fold Study Group, Comparison of smooth-gel hyaluronic acid dermal fillers with cross-linked bovine collagen: a multicenter, double-masked, randomized, within-subject study." Dermatol. Surg. 33(Suppl 2): S128-S135 (2007).
Beasley et al. :Hyaluronic acid fillers: a comprehensive review. Facial Plast. Surg. 25(2): 86-94 (2009).
Beer "Dermal fillers and combinations of fillers for facial rejuvenation." Dermatol. Clin. 27(4): 427-432 (2009).
Belda, Jose L, et al., "Hyaluronic acid combined with mannitol to improve protection against free-radical endothelial damage: Experimental Model," J.Cataract Refract Surg 2005; 31:1213-1218.
Bircher, Andreas J., et al., "Delayed-type hypersensitivity to subcutaneous lidocaine with tolerance to articaine: confirmation by in vivo and in vitro tests", Contact Dermatitis 1996, 34, 387-389.

Bluel et al., "Evaluation of Reconstituted Collagen Tape as a Model for Chemically Modified Soft Tissues", Biomat. Med. De. Art. Org., 9(1):37-46 (1981).
Buck et al, "Injectable Fillers for our Facial Rejuvenation: a Review", Journal of Plastic, Reconstructive and Aesthetic Surgery, (2009), 62:11-18, XP002668828.
Capozzi et al., "Distant Migration of Silicone Gel From a Ruptured Breats Implant", Plastic and Reconstructive Surgery, 1978; 62:302-3.
Carlin, G., et al., "Effect of anti-inflammatory drugs on xanthine oxidase and xanthine oxidase induced depolymerization of hyaluronic acid," Agents and Actions. 16 (5):377-384 (1985).
Carruthers et al. "The science and art of dermal fillers for soft-tissue augmentation." J. Drugs Dermatol. 8(4): 335-350 (2009).
Champion, et al., "Role of Target Geometry in Phagocytosis", S. Proc. Nat. Acad. Sci., Mar. 2008, 2006, vol. 103, No. 13, pp. 4930-4934.
Chin, Thomas M., et al., "Allergic Hypersensitivity to Lidocaine Hydrochloride", International journal of Dermatology, vol. 19, Apr. 1980, pp. 147-148.
Chvapil, "Collagen Sponse: Theory and Practice of Medical Applications", J. Biomed Mater. Res., II, pp. 721-741 (1977).
Clark et al., "The Influence of Triamcinolone Acetonide on Joint Stiffness in the Rat", J Bone Joint Surg Am, 1971; 53:1409-1414.
Cohen et al., "Organization and Adhesive Properties of the Hyaluronan Pericellular Coat of Chondrocytes and Epithelial Cells", Biophys J., 2003; 85:1996-2005.
Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.
Deland, "Intrathecal Toxicity Studies with Benzyl Alcohol", Toxicol Appl Pharmacol, 1973; 25(2):153.
Desai et al., J Pharm Sci Feb. 1995; 84 (2): 212-5.
Eyre et al., Top Curr. Chem., 2005, vol. 247, pp. 207-229.
Falcone et al. "Crosslinked hyaluronic acid dermal fillers: a comparison of rheological properties." J Biomed Mater Res A. 87(1): 264-271 (2008).
Falcone et al. "Temporary polysaccharide dermal fillers: a model for persistence based on physical properties." Dermatol Surg. 35(8): 1238-1243 (2009).
Farley, Jon S., et al., "Diluting Lidocaine and Mepivacaine in Balanced Salt Solution Reduces the Pain of Intradermal Injection", Regional Anesthesia 19(1):48-51, 1994.
Frati, Elena, et al., "Degradation of hyaluronic acid by photosensitized riboflavin in vitro. Modulation of the effect by transition metals, radical quenchers, and metal chelators," Free Radical Biology Medicine 22 (7):1139-1144 (1997).
Fujinaga, Masahiko, et al., "Reproductive and Teratogenic Effects of Lidocaine in Sprague-Dawley Rats", Anesthesiology 65:626-632, 1986.
Gammaitoni, Arnold R., et al., "Pharmacokinetics and safety of continuously applied lidocaine patches 5%", Am J Health Syst Pharm, vol. 59, Nov. 15, 2002, pp. 2215-2220.
GinShiCel MH Hydroxy Propyl methyl Cellulose, Web Page http://www.ginshicel.cn/MHPC.html, Nov. 12, 2008.
Gold MH, "Use of Hyaluronic acid fillers for the treatment of the aging face." Clin. Interventions Aging 2(3): 369-376 (2007).
Goldberg "Breakthroughs in US dermal fillers for facial soft-tissue augmentation." J Cosmet Laser Ther. 11(4): 240-247 (2009).
Graefe, Hendrik, et al., "Sensitive and specific photometric determination of mannitol in human serum," Clin Chem Lab Med. 41 (8):1049-1055 (2003).
Grecomoro et al., "Intra-Articular Treatment with Sodium Hyaluronate in Gonarthrosis" A Controlled Clinical Trial Versus Placebo, Pharmatherapeutica, 1987; 5(2):137-41.
Grillo et al., "Thermal Reconstitution of Collagen from Solution and the Response to Its Heterologous Implantation", JSR II, No. 1, pp. 69-82 (1962).
Hassan et al., Effects of Adjuvants to local anaesthetics on their duration. III. Experimental studies of hyaluronic acid. Abstract Pub Med [Acta Anesthesiol Scand. May 1985; 29(4):384-8].

(56) References Cited

OTHER PUBLICATIONS

Hayashibara, "AA2G"; Sep. 23, 2007, http://web.archive.org/web/20079230720l0/http://www.hayashibara-intl.com/cosmetics/aa2g.html.
Helary et al., "Concentrated collagen hydrogels as dermal substitutes", Biomaterials 31 (2010) 481-490.
Helliwell, "Use of an Objective Measure of Articular Stiffness to Record Changes in Finger Joints After Intra-Articular Injection of Corticosteroid", An Theum Dis, 1997; 56:7.
Hertzberger-Ten et al., "Intra-Articular Steroids in Pauciarticular Juvenile Chronic Arthritis", Type I, Eur J Ped 1991; 150:170-172.
Hetherington, "Potential for Patient Harm From Intrathecal Administration of Preserved Solutions", Med J Aust, 2000, 173(3):p. 141.
Hurst, "Adhesive Arachnoiditis and Vascular Blockage Caused by Detergents and Other Chemical Iriitants: an Experimental Study", J Path Bact, 1955; 70:167.
Intramed Mannitol 20% m/v Infusion, package insert, pp. 1-2 (2010) http://home.intekom.com/pharm/intramed/manitl20.html.
Jones et al., "Intra-Articular Hyaluronic Acid Compared to Intra-Articular Triamcinolone Hexacetonide in Inflammatory Knee Osteoarthritis", Osteoarthritis Cartilage, 1995, 3:269-273.
Kablik et al. "Comparative physical properties of hyaluronic acid dermal fillers." Dermatol. Surg. Suppl. 35(Suppl. 1): 302-312 (2009).
Klein, "Skin Filling Collagen and Other Injectables of the Skin", Dermatologic Clinics, Jul. 2001, vol. 19, No. 3, pp. 491-588, ix, XP00919589.
Kopp et al., The Short-Term Effect of Intra-Articular Injections of Sodium Hyaluronate and Corticosteroid on Temporomandibular Joint Pain and Dysfunction, J. Oral Maxilofac.
Kulicke et al., "Visco-Elastic Properties of Sodium Hyaluronate Solutions," American Institue of Physics (2008).
Bleyer, Mark, SIS Facial Implant 510(k) Summary, Cook Biotech Inc., May 19, 2005.
Kulicke, Werner-Michael et al., Visco-Elastic Properties of Sodium Hyaluronate Solutions, Institute for Technical and Macromolecular Chemistry, 2008, 585-587, DE.
Niamtu III, DMD, Joseph, Advanta Facial Implants, Oral Maxillofacial Surg Clin N Am, 2005, 29-39, 17.
Truswell, MD, William H., Dual-Porosity Expanded Polytetrafluoroethylene Soft Tissue Implant, Arch Facial Plast Surg, Apr. 2002, 92-97, 4(2).
Laeschke, "Biocompatibility of Microparticles into Soft Tissue Fillers", 23 Semin. Cutan. Med. Surg., 214 (2004).
Lamar et al., "Antifibrosis Effect of Novel Gels in Anterior Ciliary Sclerotomy ACS)," ARVO 2002 abstract.
Levy, Jaime et al., "Lidocaine hypersensitivity after subconjunctival injection", Can J Ophthalmol 2006; 41:204-6.
Lindvall et al.; "Influence of Various Compunds on the Degradation of Hyaluronic Acid by a Myeloperoxidase System"; Chemico-Biological Interactions; vol. 90; pp. 1-12; 1994.
Lupo, MP., "Hyaluronic acid fillers in facial rejuvenation." Semin. Cutan. Med. Surg. 25(3): 122-126 (2006).
Mackley, et al., "Delayed-Type Hypersensitivity to Lidocaine", Arch Dermatol, vol. 139, Mar. 2003, pp. 343-346.
Mancinelli et al., "Intramuscular High-Dose Triamcinolone Acetonide in the Treatment of Severe Chronic Asthma", West J. Med, Nov. 1997: 167(5), 322-329.
Matsumoto, Alan H, et al., "Reducing the Discomfort of Lidocaine Administration through pH Buffering," Journal of Vascular and Interventional Radiology, Jan.-Feb. 1994, pp. 171-175.
McCarty et al., "Inflammatory Reaction After Intrasynovial Injection of Microcrystalline Adrenocorticosteroid Esters", Arthritis and Rheumatism, 7(4):359-367 (1964).
McCleland, Plastic Reconstructive Surgery, 100(6), Nov. 1997, pp. 1466-1474.
McPherson, John M., "Development and Biochemical Characterization of Injectable Collagen," J. Dermatol Surg Oncol, 14 (Supp)1):7 Jul. 1988, pp. 13-20.

Millay et al.; "Vasoconstrictors in Facial Plastic Surgery"; Archives of Otolaryngology-Head & Neck Surgery; vol. 117; pp. 160-163; Feb. 1991.
Orvisky, E., et al., "High-molecular-weight hyaluronan—a valuable tool in testing the antioxidative activity of amphiphilic drugs stobadine and vinpocetine," Pharm.Biomed.Anal. 16:419-424 (1997).
Osmitrol (generic name Mannitol),Official FDA Information, side effects and uses, pp. 1-10 (2010) http://www.drugs.com/pro/osmitrol.html.
Park et al., "Biological Characterization of EDC-crosslinked Collagen-Hyaluronic Acid Matrix in Dermal Tissue Restoration", Biomaterials 24 (2003) 1631-1641.
Park et al., "Characterization of Porous Collagen/Hyaluronic Acid Scaffold Modified by 1-ethy1-3-(3-dimethylaminopropyl)carbodiimide cross-linking", Biomaterials 23 (2002): 1205-1212.
Powell; "Stability of Lidocaine in Aqueous Solution: Effect of Temperature, pH, Buffer, and Metal Ions on Amide Hydrolysis"; Pharmaceutical Research; vol. 4, No. 1, 1987.
Prestwich, Glenn D., "Evaluating drug efficacy and toxicology in three dimensions: using synthetic extracellular matrices in drug discovery," Accounts of Chemical Research 41 (1):139-148 (2008).
Rehakova, Milena, et al., "Properties of collagen and hyaluronic acid composite materials and their modifications by chemical crosslinking," Journal of Biomedical Research, vol. 30, 1996, pp. 36-372, XP002590342.
Remington's Pharmaceutical Science Mac Publishing Company, Easton, PA 16th Edition 1980.
Rosenblatt et al., "The Effect of Collagen Fiber Size Distribution on the Release Rate of Proteins from Collagen Matrices by Diffusion", J. Controlled Rel., 9, pp. 195-203 (1989).
Rosenblatt et al., "Chain Rigidity and Diffusional Release in Biopolymer Gels", Proceed. Inter. Symp. Control. Rel. Bioact. Mater., 20, pp. 264-265 (1993) Controlled Release Society, Inc.
Sannino et al., "Crosslinking of Cellulose Derivatives and Hyaluronic Acid with Water-Soluble Carbodiimide," Polymer 46 (2005)pp. 11206-11212.
SCULPTRA® Aesthetic (injectable poly-L-lactic acid) Directions for Use, Dermik Laboratories product insert (Jul. 2009), sanofi-aventis U.S. LLC.
Segura et al. "Crosslinked hyaluronic acid hydrogels: a strategy to functionalize and pattern." Biomaterials 26(4): 359-371 (2005).
Selvi et al, "Arthritis Induced by Corticosteroid Crystals", J. Rheumatology, 2004, 34:3.
Serban et al. "Modular Extracellular Matrices: Solutions for the Puzzle." Methods 45(1): 93-98 (2008).
Shu et al. "Synthesis and evaluation of injectable, in situ crosslinkable synthetic extracellular matrices for tissue engineering." J. Biomed. Mater. Res. A. 79(4): 902-912 (2006).
Silver et al., "Physical Properties of Hyaluronic Acid and Hydroxypropylmethylcellulose in Solution: Evaluation of Coating Ability," Journal of Applied Biomaterials, vol. 5, 89-98 (1994).
Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers by; vol. 31, No. 24; pp. 6173-6181; Aug. 1, 2010.
Smith, Kevin C., et al., "Five Percent Lidocaine Cream Applied Simultaneously to Skin and Mucosa of the Lips Creates Excellent Anesthesia for Filler Injections", Dermatol Surg 2005; 31:1635-1637.
Park et al., "In vireio evaluation of conjugated Hyaluronic acid with Ascorbic Acid", Journal of Bone & Joint Surgery, British vol. 92-B, XP-002706399, 2010.
TRB Chemedica Ophthalmic Line, Visiol, product info., pp. 1-2.
Visiol, Viscoelstic gel for use in ocular surgery, (2010) p. 1, htt://www.trbchemedica.com/index.php/option=com_content&tas.
Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.

(56) References Cited

OTHER PUBLICATIONS

Wahl, "European Evaluation of a New Hyaluronic Acid Filler Incorporating Lidocaine", Journal of Cosmetic Dermatology; vol. 7; pp. 298-303; 2008.

Weidmann; "New Hyaluronic Acid Filler for Subdermal and Long-Lasting Volume Restoration of the Face"; European Dermatology; pp. 65-68; 2009.

Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.

Yeom et al. "Effect of Cross-Linking Reagents for Hyaluronic Acid Hydrogel Dermal Fillers on Tissue Augmentation and Regeneration." Bioconjugate Chem., 21(2): 240-247 (2010).

Yui, Nobuhiko, et al., "Inflammation responsive degradation of crosslinked hyaluronic acid gels," Journal of Controlled release, 22 (1992) pp. 105-116.

Yui, Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.

Yun, YH et al. "Hyaluronan Microspheres for Sustained Gene Delivery and Site-Specific Targeting", Biomaterials, vol. 25, 2004, pp. 147-157.

Zheng et al. "In situ crosslinkable hyaluronan hydrogels for tissue engineering." Biomaterials 25(7-8): 1339-1348 (2004).

Zulian et al., Triamcinolone Acetonide and Hexacetonide Intra-Articular Treatment of Symmetrical Joints in Juvenile Idiopathic Arthritis: a Double- Blind Trial, Rheum 2004.

Boulle et al., "Lip Augmentation and Contour Correction With a Ribose Cross-linked Collagen Dermal Filler", Journals of Drugs in Dermatology, Mar. 2009, vol. 8, Issue 3, pp. 1-8.

Crosslinking Technical Handbook, Thermo Scientific, pp. 1-48, published Apr. 2009.

U.S. Appl. No. 14/126,741, filed Mar. 17, 2014.
U.S. Appl. No. 61/778,008, filed Mar. 12, 2013.
U.S. Appl. No. 61/778,066, filed Mar. 12, 2013.
U.S. Appl. No. 61/932,016, filed Jan. 27, 2014.
U.S. Appl. No. 61/932,164, filed Jan. 27, 2014.

"Thread augmentation for facial rhytides" by Conley et al., Ann. Plast. Surg. 3 118-26 (1979) (PubMed Abstract No. 396849).

U.S. Appl. No. 13/581,902, Jan. 26, 2011.
PCT/US2012/059618, Oct. 10, 2012, Tautona Group LP.

Andre, Hyaluronic Acid and Its Use as a "Rejuvenation" Agent in Cosmetic Dermatology, Seminars in Cutaneous Medicine and Surgery, 2004, vol. 23, Issue 4, pp. 218-222.

Conley et al., Thread Augmentation for Facial Rhytides, Annals of Plastic Surgery, Aug. 1979, vol. 3, No. 2, pp. 118-126.

Elvassore et al., Production of Different Morphologies of Biocompatible Polymeric Materials by Supercritical $CO_2$ Antisolvent Techniques, Biotechnology and Bioengineering, 2001, vol. 73, Issue 6, pp. 449-457.

International Search Report and Written Opinion for PCT/US2011/056216 dated Dec. 14, 2011.

International Search Report and Written Opinion for PCT/US2011/056182, dated Dec. 27, 2011.

International Search Report and Written Opinion for PCT/US2012/059618 dated Dec. 11, 2012.

International Search Report for PCT/US09/55704, dated Oct. 13, 2009.

International Search Report for PCT/US11/22636, dated Jun. 16, 2011.

International Search Report for PCT/US11/22640, dated Jun. 16, 2011.

Lapcik et al., Structure, Properties and Applications, Chemical Review, 1998, vol. 98, Issue 8, pp. 2663-2684.

Leach et al., Hyaluronan, In: Encyclopedia of Biomaterials and BioMedical Engineering, 2004, pp. 779-789, Marcel Dekker Inc.

Rinaudo et al., Review: Main Properties and Current Applications of Some Polysaccharides as Biomaterials, Polymer International, 2008, vol. 57, Issue 3, pp. 397-430.

Tezel et al., The Science of Hyaluronic Acid Dermal Fillers, Journal of Cosmetic and Laser Therapy, 2008, vol. 10, Issue 1, pp. 35-42.

Wang et al., In Vivo Stimulation of De Novo Collagen Production Caused by Cross-linked Hyaluronic Acid Dermal Filler Injections in Photodamaged Human Skin, Arch Dermatol., 2007, vol. 143, No. 2, 5 pages.

\* cited by examiner

THREADS OF HYALURONIC ACID AND/OR DERIVATIVES THEREOF, METHODS OF MAKING THEREOF AND USES THEREOF

CROSS REFERENCE TO RELATED APPLICATIONS

This application is a National Phase application under 35 U.S.C. §371 of PCT Application PCT/US2009/055704, filed Sep. 2, 2009, which claims benefit under 35 U.S.C. §119(e) from U.S. Provisional Application Ser. No. 61/190,866, filed Sep. 2, 2008, which are hereby incorporated by reference in their entirety.

FIELD

The present invention relates generally to threads of hyaluronic acid, and/or derivatives thereof, methods of making thereof and uses thereof, for example, in aesthetic applications (e.g., dermal fillers), surgery (e.g., sutures), drug delivery, negative pressure wound therapy, moist wound dressing, etc.

BACKGROUND

Hyaluronic acid is a linear polysaccharide (i.e., non-sulfated glycosaminoglycan) consisting of a repeated disaccharide unit of alternately bonded β-D-N-acetylglucoamine and β-D-glucuronic acid (i.e., $(-4GlcUA\beta 1-3GlcNAc\beta 1-)_n$) which is a chief component of the extracellular matrix and is found, for example, in connective, epithelial and neural tissue. Natural hylauronic acid is highly biocompatible because of its lack of species and organ specificity and thus is often used as a biomaterial in tissue engineering and as a common ingredient in various dermal fillers.

Various chemically modified forms of hyaluronic acid (e.g., cross linked forms, ionically modified forms, esterified forms, etc.) have been synthesized to address a significant problem associated with natural hyaluronic acid which has poor in vivo stability due to rapid enzymatic degradation and hydrolysis. Currently, hyaluronic acid or cross linked versions thereof are used in various gel forms, for example as dermal fillers, adhesion barriers, etc.

However, substantial issues exist with the use of gels of hyaluronic acid or cross linked versions thereof. First, the force required to dispense gels of hyaluronic acid or cross linked versions thereof is non-linear which causes the initial "glob" that many physicians report when injecting hyaluronic acid or cross linked versions thereof. Second, precisely dispensing hyaluronic gels to specific locations is very difficult because such gels have little mechanical strength. Further, the gel will occupy the space of least resistance which makes its use in many applications (e.g., treatment of fine wrinkles) problematic.

Accordingly, what is needed are new physical forms of hyaluronic acid or cross linked versions thereof which can be dispensed uniformly to specific locations regardless of tissue resistance. Such new forms may have particular uses, for example, in aesthetic and surgical applications, drug delivery, wound therapy and wound dressing.

SUMMARY

The present invention satisfies these and other needs by providing, in one aspect, a thread of hyaluronic acid or salts, hydrates or solvates thereof and, in a second aspect, a thread of cross linked hyaluronic acid or salts, hydrates or solvates thereof. In some embodiments, the thread is a combination of a thread of hyaluronic acid or salts, hydrates or solvates thereof and a thread of cross linked hyaluronic acid or salts, hydrates or solvates thereof.

In a third aspect, a method of making a thread of hyaluronic acid or salts, hydrates or solvates thereof is provided. Hyaluronic acid or salts, hydrates or solvates thereof are mixed with water or a buffer to form a gel. The gel is extruded to form a thread. The thread is then dried to provide a thread of hyaluronic acid.

In a fourth aspect, a method of making a thread of cross linked hyaluronic acid or salts, hydrates or solvates thereof is provided. Hyaluronic acid or salts, hydrates or solvates thereof are mixed with water or a buffer and a cross linking agent to form a gel. The gel is extruded to form a thread. The thread is then dried to provide a thread of cross linked hyaluronic acid.

In a fifth aspect a method of treating a wrinkle in a subject in need thereof is provided. A thread of hyaluronic acid or salts, hydrates or solvates thereof or a thread of cross linked hyaluronic acid or salts, hydrates or solvates thereof or a combination thereof is attached to the proximal aspect of a needle. The distal end of the needle is inserted through the skin surface of the subject into the dermis adjacent to or within the wrinkle. The dermis of the subject in the base of the wrinkle is traversed with the needle. The needle then exits the skin surface of the subject and is pulled distally until it is removed from the skin of the subject such that the thread is pulled into the location previously occupied by the needle. The excess thread is cut from the needle at the skin surface of the subject.

In still other aspects, methods of using threads of hyaluronic acid or salts, hydrates or solvates thereof or threads of cross linked hyaluronic acid or salts, hydrates or solvates thereof or combinations thereof, for example, as dermal fillers, adhesion barriers, wound dressings including negative pressure wound dressings, sutures, etc. is provided. Further provided are methods of using threads of hyaluronic acid or salts, hydrates or solvates thereof or threads of cross linked hyaluronic acid or salts, hydrates or solvates thereof or combinations thereof, for example, in surgery, opthamology, wound closure, drug delivery, etc.

DETAILED DESCRIPTION

Definitions

Figure 1:
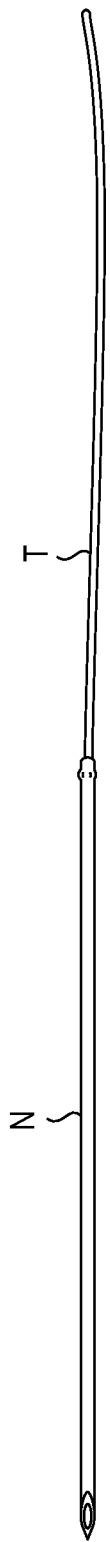
FIG. 1 illustrates a thread attached to the proximal end of a needle, in its entirety.

"Buffer" includes, but is not limited to, 2-amino-2-methyl-1,3-propanediol, 2-amino-2-methyl-1-propanol, L-(+)-tartaric acid, D-(−)-tartaric acid, ACES, ADA, acetic acid, ammonium acetate, ammonium bicarbonate, ammonium citrate, ammonium formate, ammonium oxalate, ammonium phosphate, ammonium sodium phosphate, ammonium sulfate, ammonium tartrate, BES, BICINE, BIS-TRIS, bicarbonate, boric acid, CAPS, CHES, calcium acetate, calcium carbonate, calcium citrate, citrate, citric acid, diethanolamine, EPP, ethylenediaminetetraacetic acid disodium salt, formic acid solution, Gly-Gly-Gly, Gly-Gly, glycine, HEPES, imidazole, lithium acetate, lithium citrate, MES, MOPS, magnesium acetate, magnesium citrate, magnesium formate, magnesium phosphate, oxalic acid, PIPES, phosphate buffered saline, phosphate buffered saline, piperazine potassium D-tartrate, potassium acetate, potassium bicarbonate, potassium carbonate, potassium chloride, potassium citrate, potassium formate, potassium oxalate, potassium phosphate, potassium phthalate, potassium sodium tartrate, potassium tetraborate, potassium tetraoxalate dehydrate, propionic acid solution, STE buffer solution, sodium 5,5-diethylbarbiturate, sodium acetate, sodium bicarbonate, sodium bitartrate monohydrate, sodium carbonate, sodium citrate, sodium formate, sodium oxalate, sodium phosphate, sodium pyrophosphate, sodium tartrate, sodium tetraborate, TAPS, TES, TNT, TRIS-glycine, TRIS-acetate, TRIS buffered saline, TRIS-HCl, TRIS phosphate-EDTA, tricine, triethanolamine, triethylamine, triethylammonium acetate, triethylammonium phosphate, trimethylammonium acetate, trimethylammonium phosphate, Trizma® acetate, Trizma® base, Trizma® carbonate, Trizma® hydrochloride or Trizma® maleate.

"Salt" refers to a salt of hyaluronic acid, which possesses the desired activity of the parent compound. Such salts include, but are not limited to: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, t-butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by an ammonium ion, a metal ion, e.g., an alkali metal ion (e.g., sodium or potassium), an alkaline earth ion (e.g., calcium or magnesium), or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like.

Threads of Hyaluronic Acid and Derivatives Thereof

The present invention generally provides threads of hyaluronic acid or salts, hydrates or solvates thereof, threads of cross linked hyaluronic acid or salts, hydrates or solvates thereof and combinations thereof. In some embodiments, the hyaluronic acid is isolated from an animal source. In other embodiments, the hyaluronic acid is isolated from bacterial fermentation In some embodiments, the lifetime of the threads of hyaluronic acid or salts, hydrates or solvates thereof, in vivo is between about 1 minute and about 1 month. In other embodiments, the lifetime of the thread of hyaluronic acid or salts, hydrates or solvates thereof, in vivo is between about 10 minutes and about 1 week. In still other embodiments, the lifetime of the thread of hyaluronic acid or salts, hydrates or solvates thereof, in vivo is between about 1 hour and about 3 days.

In some embodiments, the lifetime of the thread of cross linked hyaluronic acid or salts, hydrates or solvates thereof, in vivo is between about 1 week and about 24 months. In other embodiments, the lifetime of the thread of cross linked hyaluronic acid or salts, hydrates or solvates thereof, in vivo is between about 1 month and about 12 months. In still other embodiments, the lifetime of the thread of hyaluronic acid or salts, hydrates or solvates thereof, in vivo is between about 3 months and about 9 months.

In some embodiments, hyaluronic acid or salts, hydrates or solvates thereof have been cross linked with butanediol diglycidyl ether (BDDE), divinyl sulfone (DVS) or 1-ethyl-3-(3-dimethylaminopropyl) carbodiimide hydrochloride (EDC). Those of skill in the art will appreciate that many other cross linking agents may be used to crosslink hyaluronic acid or salts, hydrates or solvates thereof. Accordingly, the above list of cross linking agents is illustrative rather than comprehensive.

In some of the above embodiments, the degree of cross linking between hyaluronic acid or salts, hydrates or solvates thereof and the cross linking agent is between about 0.01% and about 20%. In other of the above embodiments, the degree of cross linking between hyaluronic acid or salts, hydrates or solvates thereof and the cross linking agent is between about 0.1% and about 10%. In still other of the above embodiments, the degree of cross linking between hyaluronic acid or salts, hydrates or solvates thereof and the cross linking agent is between about 1% and about 8%.

In some of the above embodiments, the thread includes one or more therapeutic or diagnostic agents. In other of the above embodiments, the diagnostic agent is soluble TB (tuberculosis) protein. In still other of the above embodiments, the therapeutic agent is an anesthetic, including but not limited to, lidocaine, xylocaine, novocaine, benzocaine, prilocaine, ripivacaine, propofol or combinations thereof. In still other of the above embodiments, the therapeutic agent is epinephrine, adrenaline, ephedrine, aminophylline, theophylline or combinations thereof. In still other of the above embodiments, the therapeutic agent is botulism toxin. In still other of the above embodiments, the therapeutic agent is laminin-511. In still other of the above embodiments, the therapeutic agent is glucosamine, which can be used, for example, in the treatment of regenerative joint disease. In still other of the above embodiments, the therapeutic agent is an antioxidant, including but not limited to, vitamin E or all-trans retinoic acid such as retinol. In still other of the above embodiments, the therapeutic agent includes stem cells. In still other of the above embodiments, the therapeutic agent is insulin, a growth factor such as, for example, NGF (nerve growth factor), BDNF (brain-derived neurotrophic factor), PDGF (platelet-derived growth factor) or Purmorphamine Deferoxamine NGF (nerve growth factor), dexamethasone, ascorbic acid, 5-azacytidine, 4,6-disubstituted pyrrolopyrimidine, cardiogenols, cDNA, DNA, RNAi, BMP-4 (bone morphogenetic protein-4), BMP-2 (bone morphogenetic protein-2), an antibiotic agent such as, for example, β lactams, quinolones including fluoroquinolones, aminoglycosides or macrolides, an anti-fibrotic agent, including but not limited to, hepatocyte growth factor or Pirfenidone, an anti-scarring agent, such as, for example, anti-TGF-b2 monoclonal antibody (rhAnti-TGF-b2 mAb), a peptide such as, for example, GHK copper binding peptide, a tissue regeneration agent, a steroid, fibronectin, a cytokine, an analgesic such as, for example, Tapentadol HCl, opiates, (e.g., morphine, codone, oxycodone, etc.) an antiseptic, alpha- beta or gamma-interferon, EPO, glucagons, calcitonin, heparin, interleukin-1, interleukin-2, filgrastim, a protein, HGH, luteinizing hormone, atrial natriuretic factor, Factor VIII, Factor IX, or a follicle-stimulating hormone. In still other of the above embodiments, the thread contains a combination of more than one therapeutic agent or diagnostic agent. In some of these embodiments, different threads comprise different therapeutic agents or diagnostic agents.

In some of the above embodiments, the thread has an ultimate tensile strength of between about 0 kpsi and about 250 kpsi. In other of the above embodiments, the thread has an ultimate tensile strength of between about 1 kpsi and about 125 kpsi. In still other of the above embodiments, the thread has an ultimate tensile strength of between about 5 kpsi and about 100 kpsi.

In some of the above embodiments, the thread has an axial tensile strength of between about 0.01 lbs and about 10 lbs. In other of the above embodiments, the thread has an axial tensile strength of between about 0.1 lbs and about 5 lbs. In still other of the above embodiments, the thread has an axial tensile strength of between about 0.5 lbs and about 2 lbs.

In some of the above embodiments, the thread has a cross-section area of between about $1*10^6$ in$^2$ and about $1,000*10^6$ in$^2$. In other of the above embodiments, the thread has a cross-section area of between about $10*10^6$ in$^2$ and about $500*10^6$ in$^2$. In still other of the above embodiments, the thread has a cross-section area of between about $50*10^6$ in$^2$ and about $250*10^6$ in$^2$.

In some of the above embodiments, the thread has a diameter of between about 0.0001 in and about 0.100 in. In other of the above embodiments, the thread has a diameter of between about 0.001 in and about 0.020 in. In still other of the above embodiments, the thread has a diameter of between about 0.003 and about 0.010 in.

In some of the above embodiments, the thread has an elasticity of between about 1% and 200%. In other of the above embodiments, the thread has an elasticity of between about 5% and about 100%. In still other of the above embodiments, the thread has an elasticity of between about 10% and 50%. Herein, elasticity is the % elongation of the thread while retaining ability to return to the initial length of the thread.

In some of the above embodiments, the thread has a molecular weight of between about 0.1 MD and about 8 MD (MD is a million Daltons). In other of the above embodiments, the thread has a molecular weight of between about 0.5 MD to about 4 MD. In still other of the above embodiments, the thread has a molecular weight of between about 1 MD to about 2 MD.

In some of the above embodiments, the thread has a persistent chain length of between about 10 nm and about 250 nm. In other of the above embodiments, the thread has a persistent chain length of between about 10 nm and about 125 nm. In still other of the above embodiments, the thread has a persistent chain length of between about 10 nm and about 75 nm.

In some of the above embodiments, the cross-sectional area of the thread when fully hydrated swells to between about 0% to about 10,000%. In other of the above embodiments, the cross-sectional area of the thread when fully hydrated swells to between about 0% to about 2,500%. In still other of the above embodiments, the cross-sectional area of the thread when fully hydrated swells to between about 0% to about 900%.

In some of the above embodiments, the thread elongates when fully hydrated to between about 0% to about 1,000%. In other of the above embodiments, the thread elongates when fully hydrated to between about 0% to about 100%. In still other of the above embodiments, the thread elongates when fully hydrated to between about 0% to about 30%.

In some of the above embodiments, the thread is fully hydrated after submersion in an aqueous environment in between about 1 second and about 24 hours. In other of the above embodiments, the thread is fully hydrated after submersion in an aqueous environment in between about 1 second and about 1 hour. In still other of the above embodiments, the thread is fully hydrated after submersion in an aqueous environment in between about 1 second to about 5 minutes.

In some embodiments, the thread is cross linked and has an ultimate tensile strength of between about 50 kpsi and about 75 kpsi, a diameter of between 0.005 in and about 0.015 in, the thickness or diameter of the thread when fully hydrated swells between about 50% to about 100% and the lifetime of the thread in vivo is about 6 months.

In some embodiments, braids may be formed from the threads described above. In other embodiments, cords may be formed from the threads described above. In still other embodiments, a woven mesh may be formed from the threads described above. In still other embodiments, a woven mesh may be formed from the braids or cords described above.

In some embodiments, a three-dimensional structure may be constructed by weaving or wrapping or coiling or layering the threads described above. In other embodiments, a three-dimensional structure may be constructed by weaving or wrapping or coiling or layering the braids described above. In still other embodiments, a three-dimensional structure may be constructed by weaving or wrapping or coiling or layering the cords described above. In still other embodiments, a three-dimensional structure may be constructed by weaving or wrapping or coiling or layering the meshes described above.

In some embodiments, a three-dimensional, cylindrical implant is made of any of the threads is provided. An exemplary use for such an implant is for nipple reconstruction. In some embodiments, the threads used to make the cylindrical implant are cross linked and include chondrocyte adhesion compounds. In other embodiments, the cylindrical shape is provided by multiple, concentric coils of threads.

Threads of hyaluronic acid and/or derivatives thereof may contain one or more chiral centers and therefore, may exist as stereoisomers, such as enantiomers or diastereomers. In general, all stereoisomers (i.e., all possible enantiomers and stereoisomers of the illustrated compounds including the stereoisomerically pure form (e.g., enantiomerically pure or diastereomerically pure) and enantiomeric and stereoisomeric mixtures are within the scope of the present invention.

Threads of hyaluronic acid and/or derivatives thereof may exist in several tautomeric forms and mixtures thereof all of which are within the scope of the present invention. Threads of hyaluronic acid and/or derivatives thereof may exist in unsolvated forms as well as solvated forms, including hydrated forms. In general, hydrated and solvated forms are within the scope of the present invention. Accordingly, all physical forms of threads of hyaluronic acid and/or derivatives thereof are equivalent for the uses contemplated by the present invention and are intended to be within the scope of the present invention.

Methods of Making Threads of Hyaluronic Acid and Derivatives Thereof

The present invention also provides methods for making threads of hyaluronic acid and derivatives thereof as described above. In some embodiments, a method of making threads of hyaluronic acid or salts, hydrates or solvates thereof, is provided Hyaluronic acid or salts, hydrates or solvates thereof are mixed with water or a buffer to form a gel. The gel is then extruded to form a thread of gel. The gel can be extruded, for example, by placing the gel in a syringe with a nozzle, pressurizing the syringe, and linearly translating the syringe as gel is extruded from the nozzle. Nozzle characteristics such as taper, length and diameter, the syringe pressure, and the speed of linear translation may be adjusted to make threads of different sizes and mechanical characteristics. Another method of making a thread of gel is by rolling the gel, i.e., like dough, or by placing it into a mold. Still another method of making a thread of gel is to allow the gel to stretch into a thread under the influence of gravity or using centrifugal force. Still another method of making a thread of gel is by shearing the gel in between charged parallel glass plates. Yet another method of making a thread of gel is by confining the gel into a groove patterned on an elastomer and then stretching the elastomer. Yet another method of making a thread of gel is by confining the gel into a permeable tubular structure that allows dehydration of the thread, and if necessary controlling the nature of the dehydration by adjusting environmental parameters such as temperature, pressure and gaseous composition. The thread of hyaluronic acid or salts, hydrates or solvates thereof is then dried after preparation.

In other embodiments, a method of making threads of cross linked hyaluronic acid or salts, hydrates or solvates thereof, is provided. Hyaluronic acid or salts, hydrates or solvates thereof are mixed with water or a buffer and a cross linking agent to form a gel. The gel is then extruded to form a thread as described above or the thread can be made by any of the methods described above. Generally, the gel should be extruded or otherwise manipulated soon after addition of the cross linking agent so that cross linking occurs as the thread dries. The thread of cross linked hyaluronic acid or salts, hydrates or solvates thereof is then dried after preparation.

In some embodiments, the ratio of cross linking agent to hyaluronic acid is between about 0.01% and about 10%. In other embodiments, the ratio of cross linking agent to hyaluronic acid is between about 0.02% and about 5%. In still other embodiments, the ratio of cross linking agent to hyaluronic acid is between about 0.1% and about 3%.

In some of the above embodiments, one or more therapeutic or diagnostic agents are included in the gel forming step.

In some of the above embodiments, the gel has a concentration by weight of hyaluronic acid of between about 0.1% and about 10%. In other of the above embodiments, the gel has a concentration by weight of hyaluronic acid of between about 1% and about 7%. In still other of the above embodiments, the gel has a concentration by weight of hyaluronic acid of between about 4% and about 6%.

In some of the above embodiments, the polymer chains are further oriented along the axis of the thread by being stretched axially. In other of the above embodiments, the polymer chains are oriented along the axis of the thread by gravimetric force or centrifugal force. In still other of the above embodiments, gravimetric force is applied by hanging the thread vertically. In still other of the above embodiments, the polymer chains are oriented along the axis of the thread by application of an electric potential along the length of the thread. In still other of the above embodiments, the polymer chains are oriented along the axis of the thread by a combination of the above methods.

In some of the above embodiments, the threads are hydrated with water and then dried again. In other of the above embodiments, the hydration and drying steps are repeated multiple times. In still other of the above embodiments, the polymer chains are oriented along the axis of the thread by being stretched axially, by application of gravimetric force or centrifugal force, by application of an electric potential along the length of the thread or by combinations thereof. In still other of the above embodiments, a therapeutic agent or a diagnostic agent or a cross linking agent is applied to the thread during the hydration step.

In some of the above embodiments, the gel is extruded over a previously made thread to provide a layered thread.

In another of the above embodiments, after the drying step, the thread is submerged or rinsed with an agent. In some of the above embodiments, the agent is a cross linking agent, therapeutic or diagnostic agent.

In another of the above embodiments, while the thread is hydrated, for example after a rinsing step, the thread is submerged or rinsed with an agent. In some of the above embodiments, the agent is a cross linking agent, therapeutic or diagnostic agent.

In still other of the above embodiments, the thread is frozen and then thawed. In still other of the above embodiments, the thread is frozen and then thawed at least more than once.

In still other of the above embodiments, a dried thread is irradiated to promote cross linking. In some of the above embodiments, a hydrated thread is irradiated to promote cross linking.

In still other of the above embodiments, a dried or hydrated thread is coated to alter the properties of the thread, with a bioabsorbable biopolymer, such as for example, collagen, PEG or PLGA. Alternatively, woven constructs, whether single layer or 3D, can be coated in their entirety to create weaves or meshes with altered physical properties from that of a free-woven mesh.

Methods of Using Threads of Hyaluronic Acid and Derivatives Thereof

The threads, braids, cords, woven meshes or three-dimensional structures described herein can be used, for example, to fill aneurysms, occlude blood flow to tumors, (i.e., tumor occlusion), in eye-lid surgery, in penile augmentation (e.g., for enlargement or for sensitivity reduction, i.e., pre-mature ejaculation treatment), inter-nasal (blood-brain barrier) delivery devices for diagnostic and/or therapeutic agents, corneal implants for drug delivery, nose augmentation or reconstruction, lip augmentation or reconstruction, facial augmentation or reconstruction, ear lobe augmentation or reconstruction, spinal implants (e.g., to support a bulging disc), root canal filler (medicated with therapeutic agent), glottal insufficiency, laser photo-refractive therapy (e.g., hyaluronic acid thread/weave used as a cushion), scaffolding for organ regrowth, spinal cord treatment (BDNF and NGF), in Parkinson's disease (stereotactic delivery), precise delivery of therapeutic or diagnostic molecules, in pulp implantation, replacement pulp root canal treatment, shaped root canal system, negative pressure wound therapy, adhesion barriers and wound dressings.

In some embodiments, the threads, braids, cords, woven meshes or three-dimensional structures described herein are used as dermal fillers in various aesthetic applications. In other embodiments, the threads, braids, cords, woven meshes or three-dimensional structures described herein are used as sutures in various surgical applications. In still other embodiments, the threads, braids, cords, woven meshes or three-dimensional structures described herein are used in ophthalmologic surgery, drug delivery and intra-articular injection.

In some embodiments, the threads, braids, cords, woven meshes or three-dimensional structures described herein are used in wound dressings including negative pressure wound dressings.

In some embodiments, wound dressing remains in contact with the wound for at least 72 hours. In other embodiments, the negative pressure wound dressing remains in contact with the wound for at least 1 week. In still other embodiments, the wound dressing remains in contact with the wound for at least 2 weeks. In still other embodiments, the wound dressing remains in contact with the wound for at least 3 weeks. In still other embodiments, the wound dressing remains in contact with the wound for at least 4 weeks. In the above embodiments, it should be understood that granulation tissue is not retaining the threads, braids, cords, woven meshes or three-dimensional structures described herein as these components are fully absorbable. In some of these embodiments, the wound dressing is between about 1 cm and about 5 cm thick. Accordingly, in some of these embodiments, wound bed closure may be achieved without changing the dressing.

In some embodiments, the woven meshes described herein are used in wound dressings including negative pressure wound dressings. In other embodiments, the dressing include between 2 and about 10 layers of woven meshes.

In still other embodiments, the woven meshes comprise identical threads. In still other embodiments, the woven meshes comprise different threads.

In some embodiments, the woven meshes are between about 1 mm and about 2 mm thick when dry. In other embodiments, the woven meshes are between about 2 mm and about 4 mm thick when dry.

In some embodiments, the pore size of the woven mesh is between about 1 mm and about 10 mm in width. In other embodiments, the pore size of the woven mesh is between about 0.3 mm and about 0.6 mm in width. In still other embodiments, the pores of the woven mesh are aligned. In still other embodiments, the pores of the woven mesh are staggered. In still other embodiments, the woven meshes are collimated to create pores of desired size.

In some embodiments, the woven mesh is mechanically stable at a vacuum up to about 75 mm Hg. In other embodiments, the woven mesh is mechanically stable at a vacuum up to about 150 mm Hg.

In some embodiments, the woven mesh includes collagen. In other embodiments, the dressing is attached to a polyurethane foam. In still other embodiments, the polyurethane foam is open celled. In still other embodiments, the dressing is attached to a thin film. In still other embodiments, the thin film is silicone or polyurethane. In still other embodiments, the dressing is attached to the thin film with a water soluble adhesive.

In some embodiments, the thread used in the dressing includes a therapeutic agent or a diagnostic agent.

In some embodiments, a negative pressure wound dressing (Johnson et al., U.S. Pat. No. 7,070,584, Kemp et al., U.S. Pat. No. 5,256,418, Chatelier et al., U.S. Pat. No. 5,449,383, Bennet et al., U.S. Pat. No. 5,578,662, Yasukawa et al., U.S. Pat. Nos. 5,629,186 and 5,780,281 and Ser. No. 08/951,832) is provided for use in vacuum induced healing of wounds, particularly open surface wounds (Zamierski U.S. Pat. Nos. 4,969,880, 5,100,396, 5,261,893, 5,527,293 and 6,071,267 and Argenta et al., U.S. Pat. Nos. 5,636,643 and 5,645,081). The dressing includes a pad which conforms to the wound location, an air-tight seal which is removably adhered to the pad, a negative pressure source in fluid communication with the pad and the threads, braids, cords, woven meshes or three-dimensional structures described herein attached to the wound contacting surface of the pad. The pad, seal and vacuum source are implemented as described in the prior art.

In other embodiments, the threads, braids, cords, woven meshes or three-dimensional structures described herein are mechanically stable at a vacuum up to about 75 mm Hg. In still other embodiments, the threads, braids, cords, woven meshes or three-dimensional structures described herein are mechanically stable at a vacuum up to about 150 mm Hg. In still other embodiments, the dressing includes at least one layer of woven mesh. In still other embodiments, the dressing include between 2 and about 10 layers of woven mesh. In still other embodiments, the pad is a foam. In still other embodiments, the pad is an open cell polyurethane foam.

In some embodiments a tube connects the pad to the negative pressure source. In still other embodiments, a removable canister is inserted between the pad and the negative pressure source and is in fluid communication with both the pad and the negative pressure source.

In some embodiments, the threads, braids, cords, woven meshes or three-dimensional structures described herein are not hydrated. Accordingly, in these embodiments, the dressing could absorb wound exudates when placed in contact with the wound. In other embodiments, the threads, braids, cords, woven meshes or three-dimensional structures described herein are hydrated. Accordingly, in these embodiments, the dressing could keep the wound moist when placed in contact with the wound.

In some embodiments, an input port attached to a fluid is connected with the pad. Accordingly, in these embodiments, fluid could be dispensed in the wound. In some embodiments, the fluid is saline. In other embodiments, the fluid contains diagnostic or therapeutic agents.

In some embodiments, the threads, braids, cords, woven meshes or three-dimensional structures described herein are used as adhesion barriers. In some embodiments, the woven meshes described herein are used in adhesion barriers.

Figure 2A:
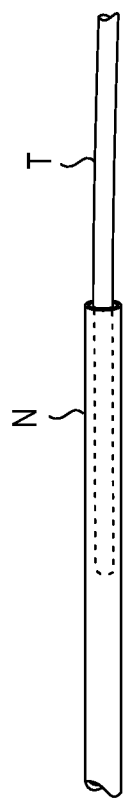
FIG. 2A illustrates a close-up view of a thread inserted into the inner-diameter of a needle.
Figure 2B:
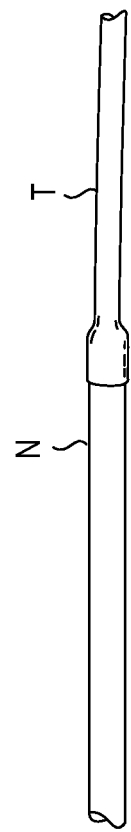
FIG. 2B illustrates a close-up view of the proximal end of a solid needle with the thread overlapping the needle.
Figure 3A:
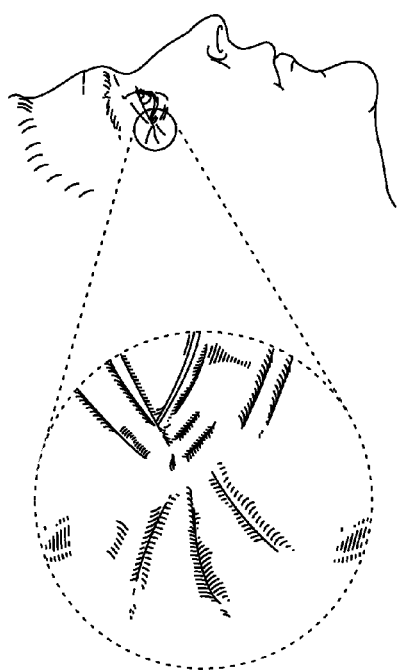
FIG. 3A illustrates a fine, facial wrinkle in the peri-orbital region of a human.
Figure 3B:
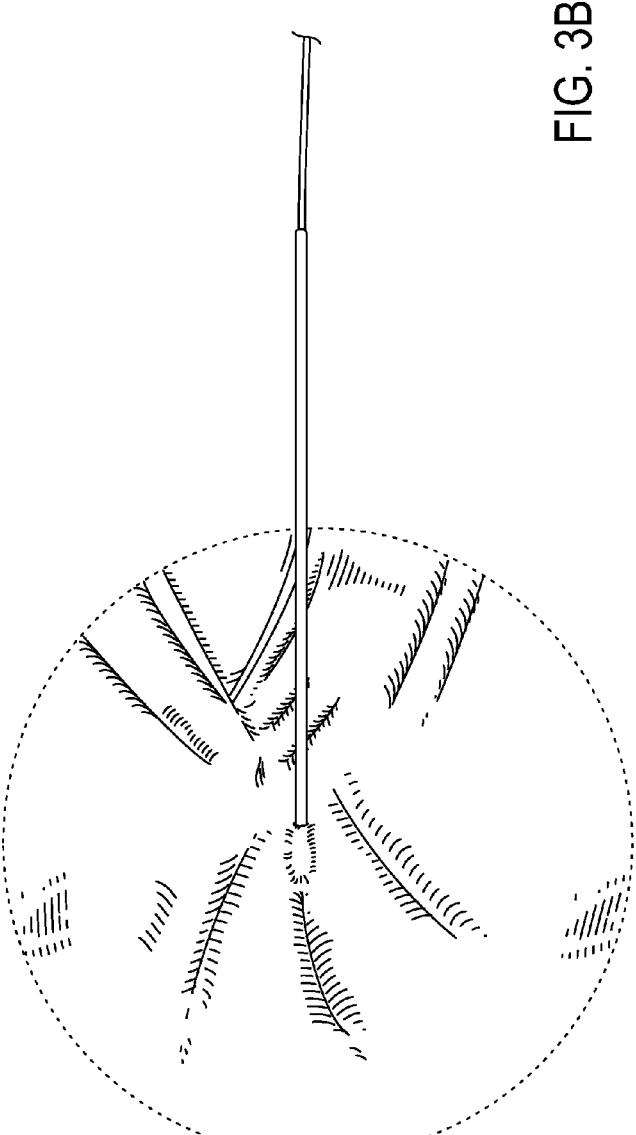
FIG. 3B illustrates a needle and thread being inserted into the dermis of the wrinkle at the medial margin.
Figure 3C:
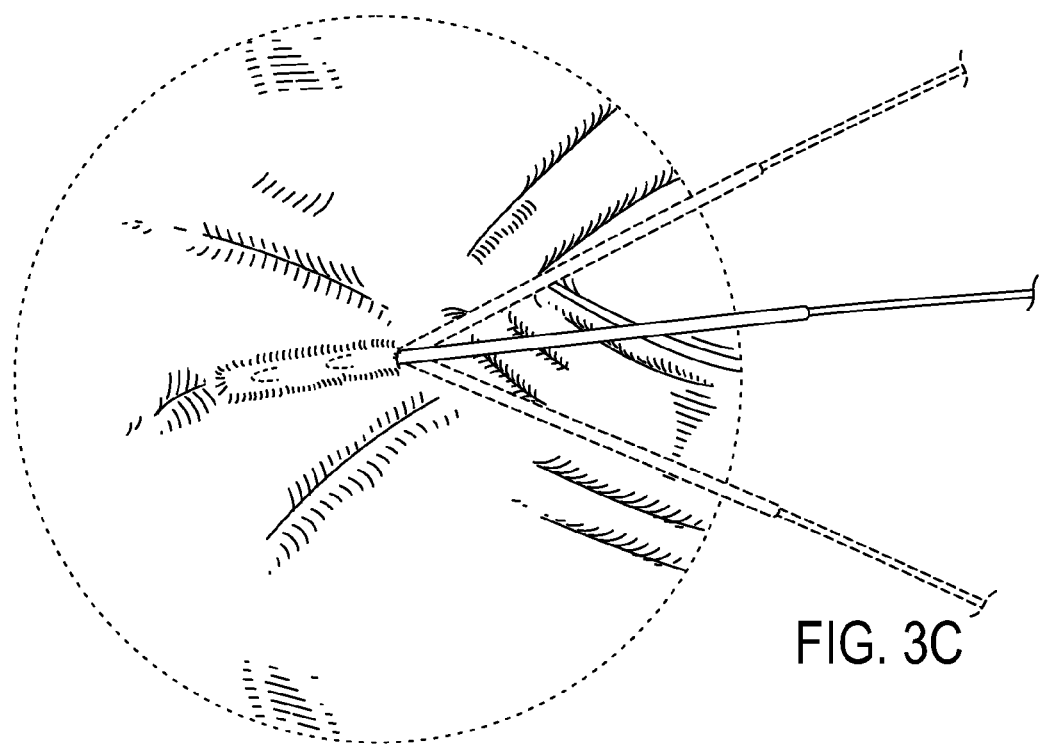
FIG. 3C illustrates the needle being adjusted to traverse beneath the wrinkle.
Figure 3D:
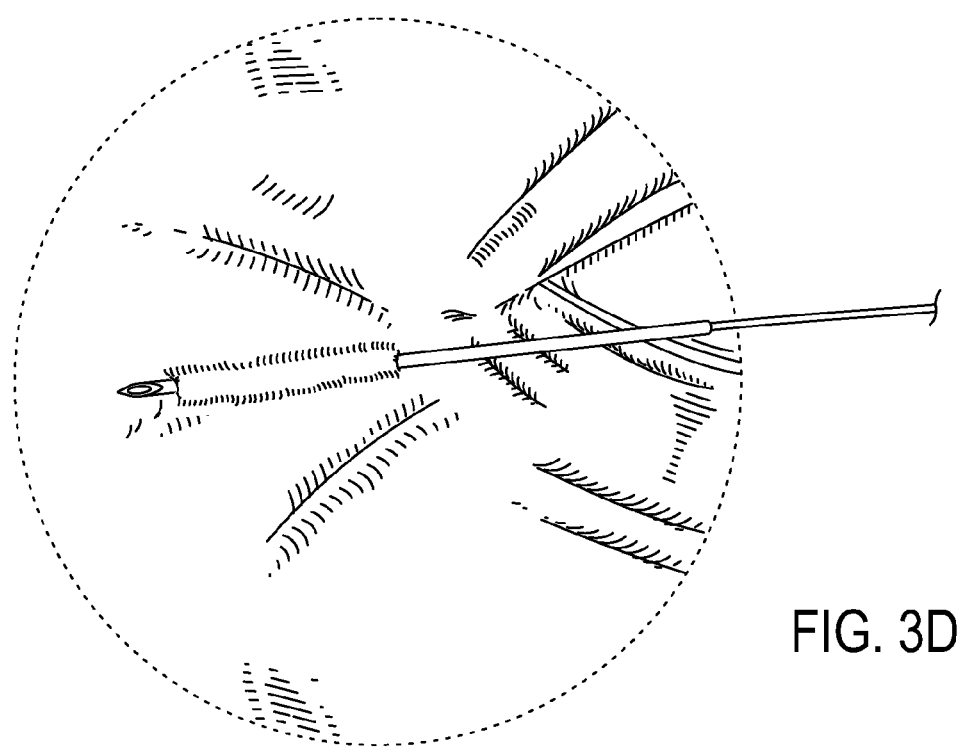
FIG. 3D illustrates the needle exiting at the lateral margin of the wrinkle.
Figure 3E:
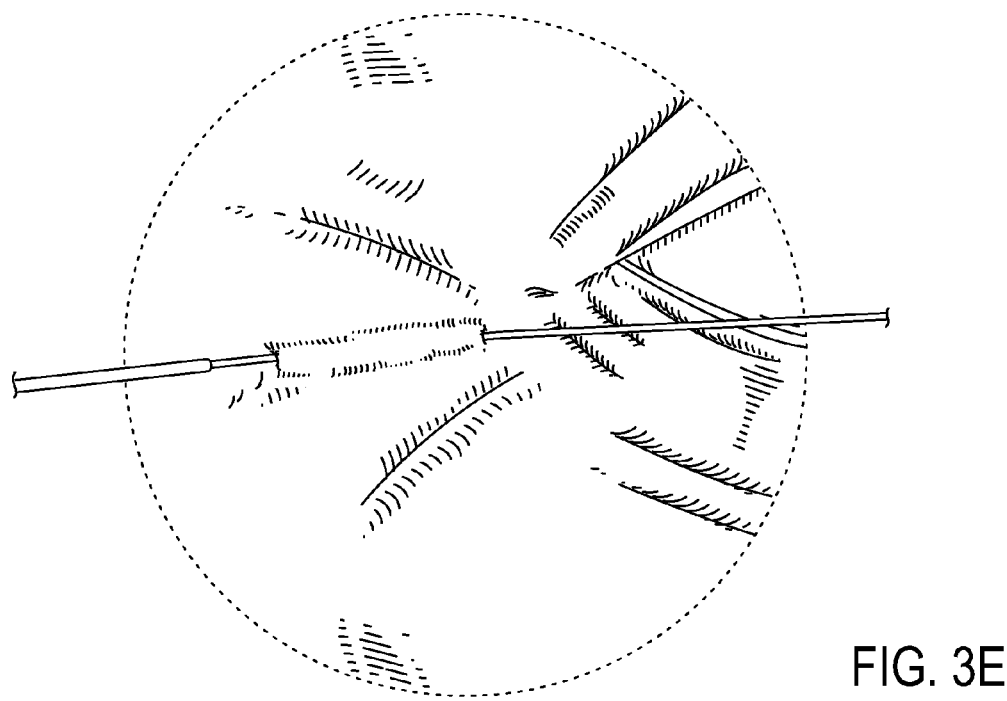
FIG. 3E illustrates the needle having pulled the thread into the location it previously occupied beneath the wrinkle.
Figure 3F:
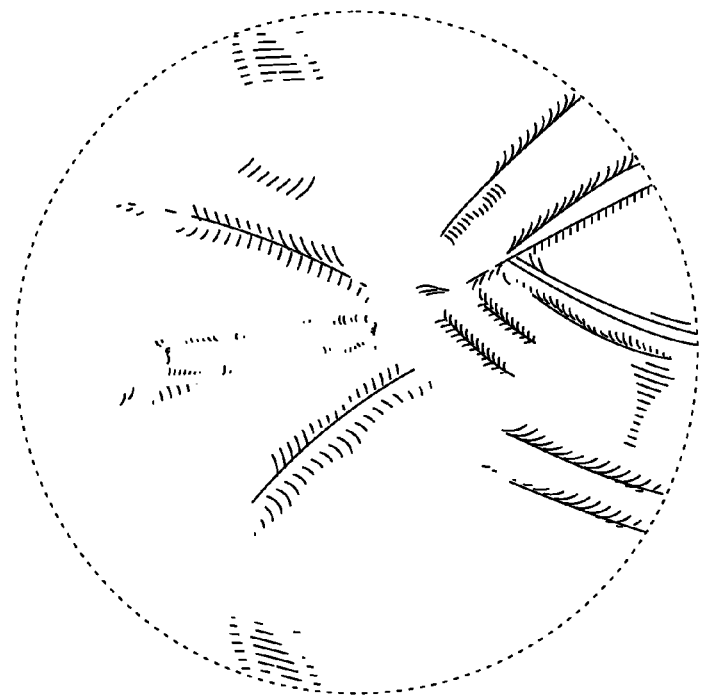
FIG. 3F illustrates the thread implanted beneath the wrinkle, with excess thread having been cut off.

In some embodiments, a method of treating a wrinkle in a subject is provided. For example, the wrinkle may be in the peri-orbital region as illustrated in FIG. 3A. The thread may be attached to a needle as illustrated, for example, in FIGS. 1, 2A and 2B. The distal end of the needle may be inserted through the skin surface of the subject into the dermis adjacent to or within the wrinkle as illustrated, for example, in FIG. 3B. In some embodiments, the thread is inserted into the subcutaneous space instead of the dermis. The needle then may traverse the dermis of the subject beneath the wrinkle as illustrated, for example, in FIG. 3C. The needle then may exit the skin of the subject at the opposite margin of the wrinkle, as illustrated, for example, in FIG. 3D. The needle may then be pulled distally until it is removed from the subject such that the thread is pulled into the location previously occupied by the needle beneath the wrinkle, as illustrated, for example, in FIG. 3E. Finally, excess thread is cut from the needle at the skin surface of the subject which leaves the thread implanted as illustrated, for example, in FIG. 3F.

Figure 5A:
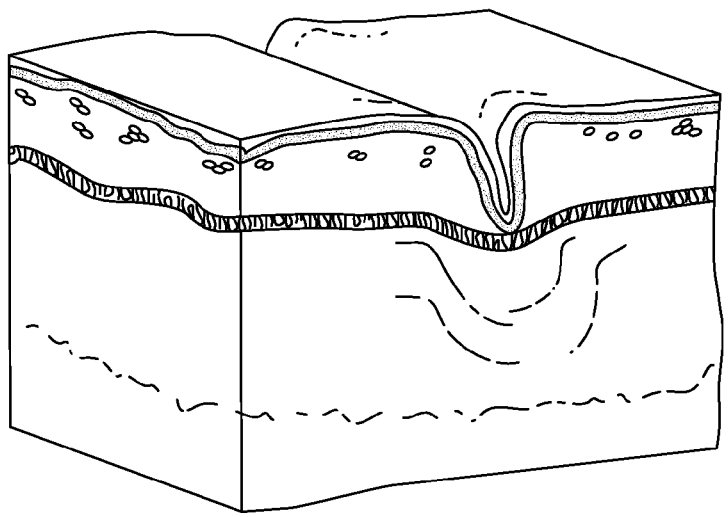
FIG. 5A illustrates a cross-sectional view of a fold or a wrinkle.
Figure 5B:
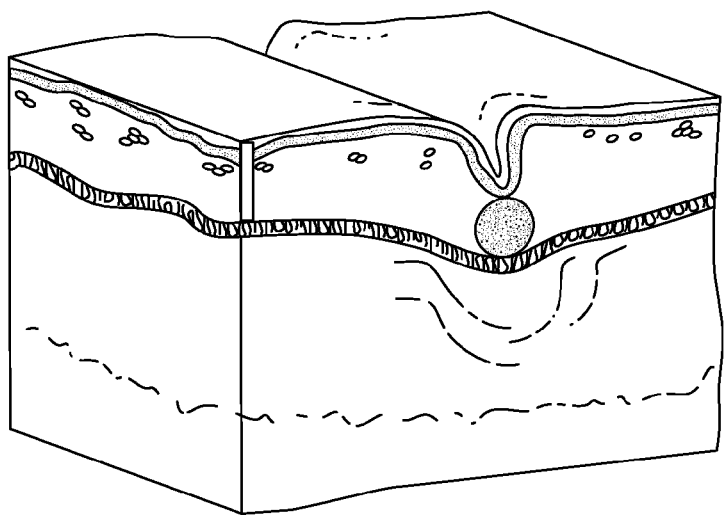
FIG. 5B illustrates a thread implanted beneath a wrinkle that is not yet hydrated.
Figure 5C:
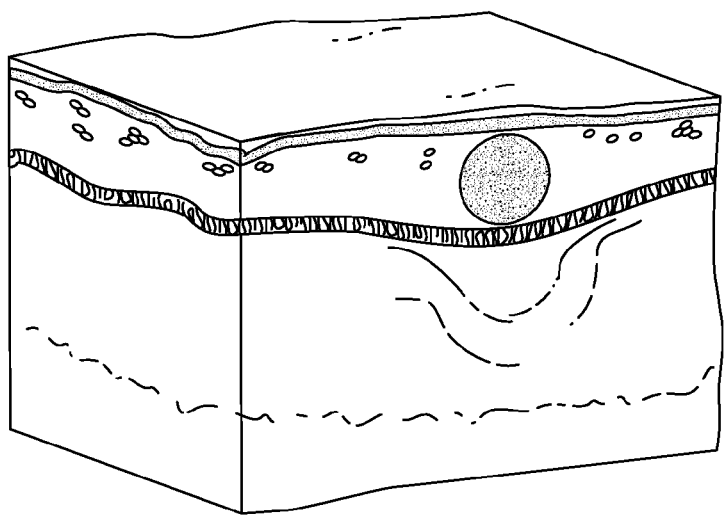
FIG. 5C illustrates a thread implanted beneath a wrinkle that is fully hydrated and has flattened the surface appearance of the wrinkle.

While not wishing to be bound by theory, the method above may successfully treat wrinkles as shown in FIGS. 5A, 5B and 5C. A typical wrinkle is illustrated in FIG. 5A. FIG. 5B illustrates a thread implanted beneath a wrinkle that is not yet hydrated. As the thread implanted beneath the wrinkle becomes fully hydrated the surface appearance of the wrinkle is concurrently flattened as illustrated in FIG. 5C.

In some embodiments, the above method may be used to rejuvenate the skin of a subject in need thereof. In many of these embodiments, the thread includes substantial amounts of non-cross linked hyaluronic acid. In some of these embodiments, the thread includes antioxidants, vitamin E or retinol or combinations thereof.

Figure 4A:
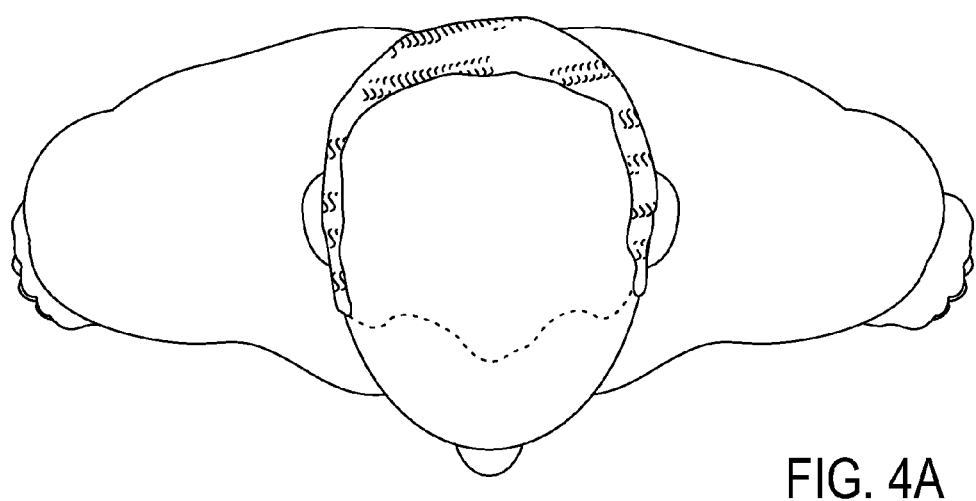
FIG. 4A illustrates a top-down view of a male with typical male-pattern baldness.
Figure 4B:
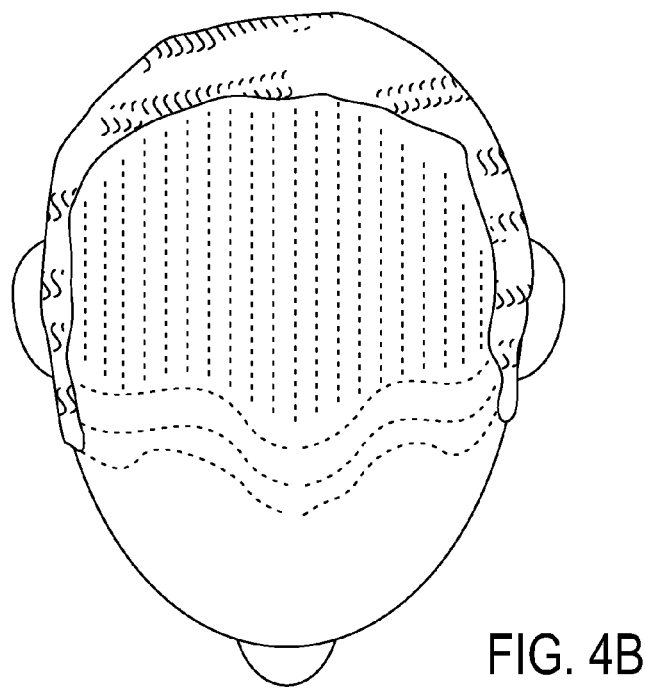
FIG. 4B illustrates where hair re-growth is desired, taking hair-lines into consideration.
Figure 4C:
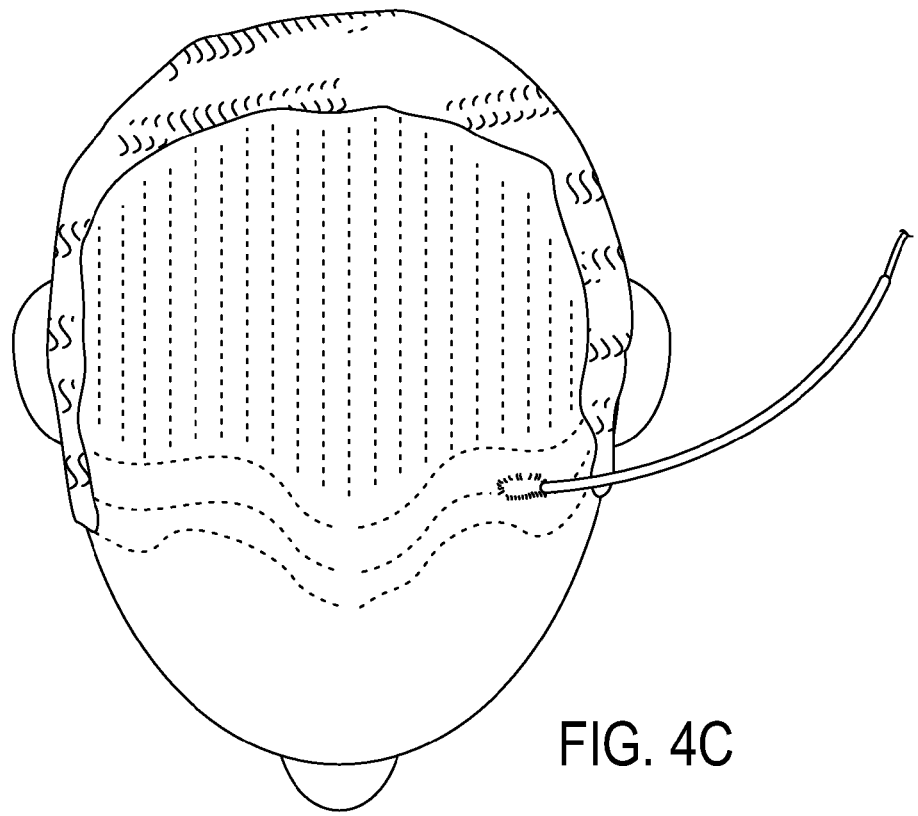
FIG. 4C illustrates a curved needle with attached thread being inserted into one imaginary line where hair re-growth is desired.
Figure 4D:
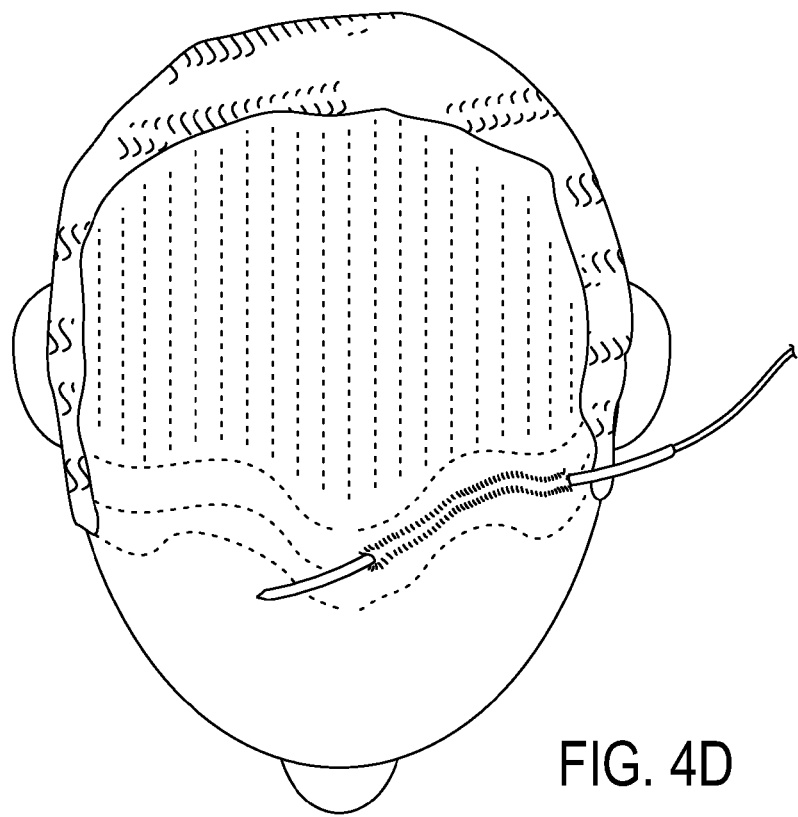
FIG. 4D illustrates the needle traversing the imaginary line, and exiting the skin.
Figure 4E:
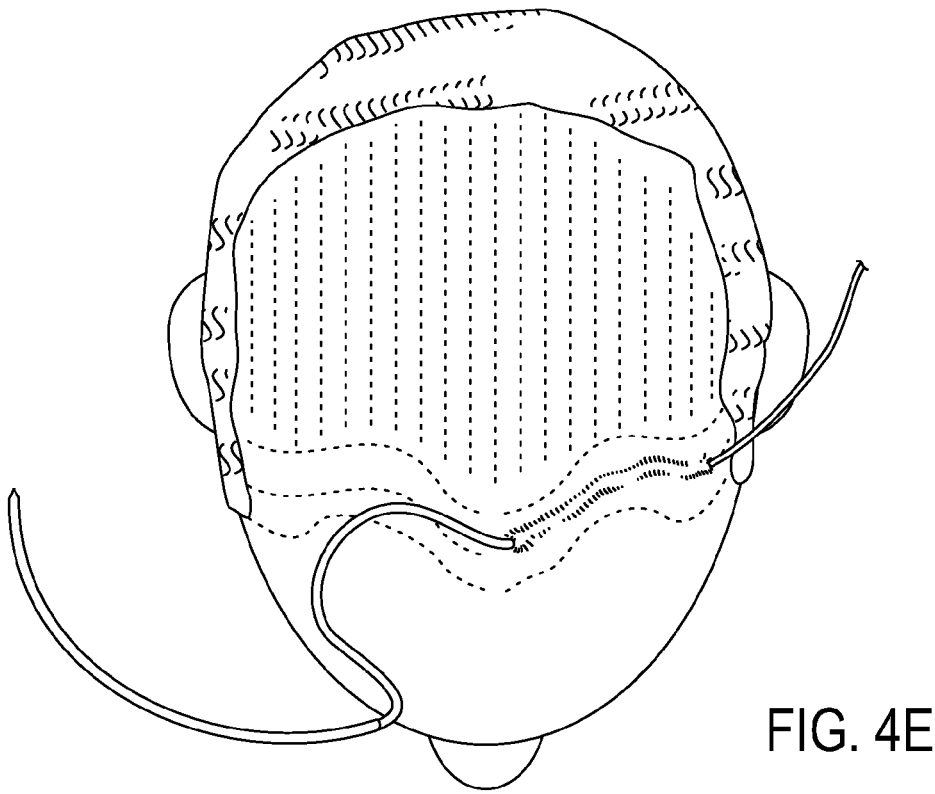
FIG. 4E illustrates the needle pulled through distally, pulling along the thread into the desired location.
Figure 4F:
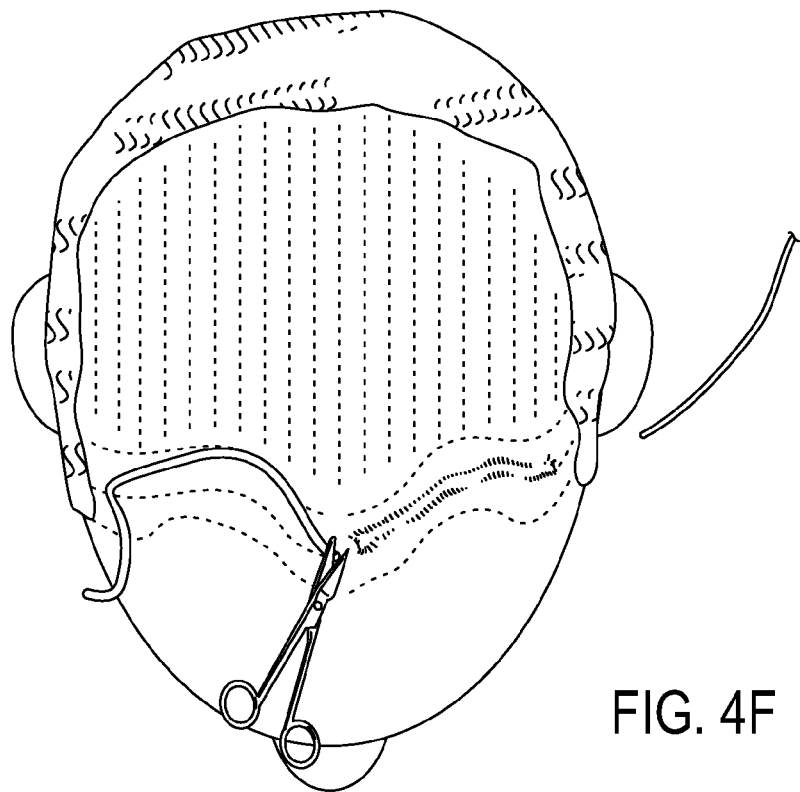
FIG. 4F illustrates scissors being used to cut excess thread.

In some embodiments, a method of treating hair loss in a subject is provided. A subject such as, for example, a male with typical male-pattern baldness is illustrated in FIG. 4A and the area where hair growth (with imaginary hairlines) is desired is shown in FIG. 4B. The thread may be attached to a needle as illustrated, for example, in FIGS. 1, 2A, 2B and 4C. The distal end of the needle may be inserted into one of the hair lines as illustrated, for example, in FIG. 4C. The needle then may traverse the area beneath the hairline of the subject and then may exit the skin of the subject as illustrated, for example, in FIG. 4D. The needle may then be pulled distally until it is removed from the subject such that the thread is pulled into the location previously occupied by the needle as illustrated, for example, in FIG. 4E. Finally, excess thread is cut from the needle at the skin surface of the subject which leaves the thread implanted as illustrated, for example, in FIG. 4D.

In some embodiments, a method for treating tumors in a subject in need thereof is provided. The thread may be attached to a needle as illustrated, for example, in FIGS. 1, 2A and 2B. The distal end of the needle may be inserted into the tumor of the subject. The needle then may traverse the tumor and then may exit the tumor. The needle may then be pulled distally until it is removed from the tumor of the subject such that the thread is pulled into the location previously occupied by the needle. Finally, excess thread is cut from the needle which leaves the thread implanted in the tumor of the subject. In some of the above embodiments, the thread includes an anti-cancer agent. In some embodiments, the thread is cross linked and includes Bcl-2 inhibitors.

Figure 6A:
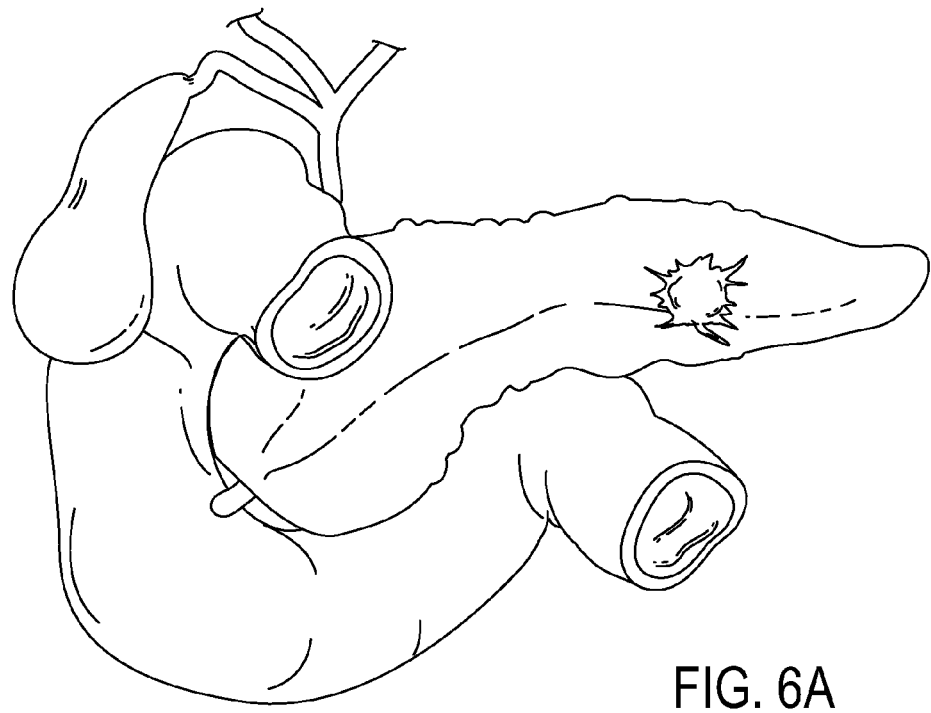
FIG. 6A illustrates a human pancreas with a tumor.
Figure 6B:
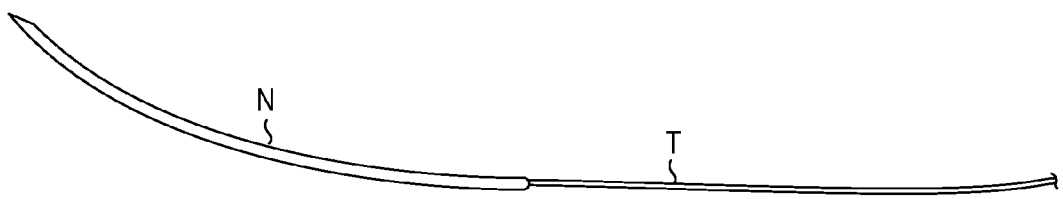
FIG. 6B illustrates a curved needle with a thread attached thereto.
Figure 6C:
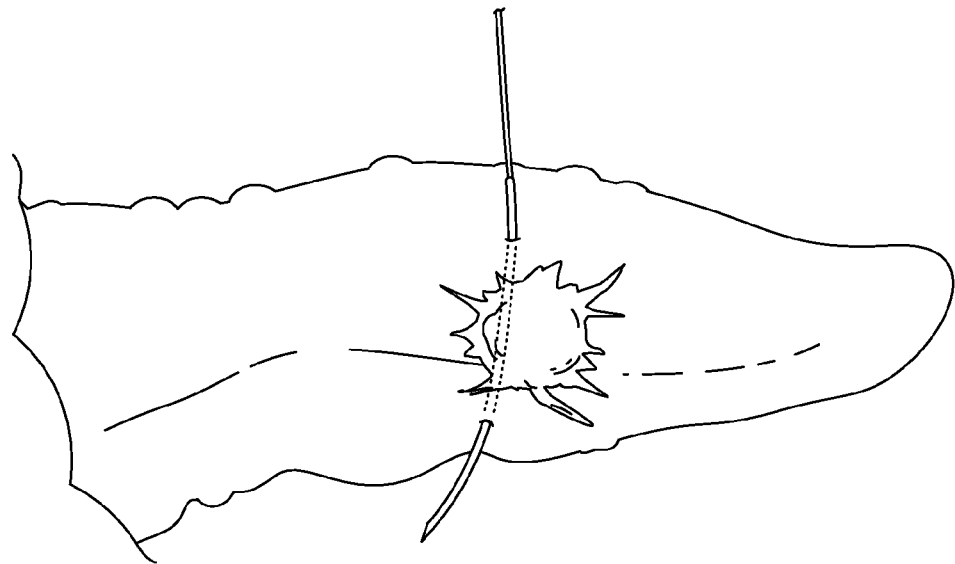
FIG. 6C illustrates a curved needle traversing the tumor within the pancreas.
Figure 6D:
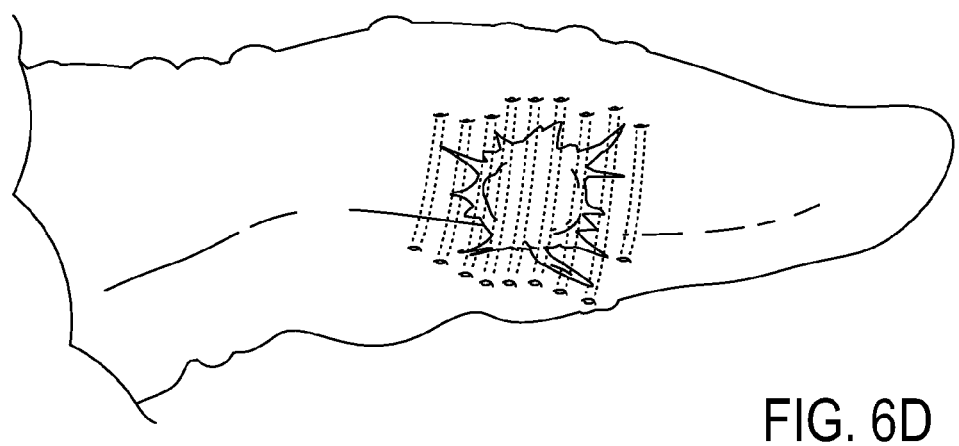
FIG. 6D illustrates the end-result of repeated implantations of thread.

In an exemplary embodiment, methods of the current invention may be used to treat pancreatic tumors. FIG. 6A illustrates a human pancreas with a tumor while FIG. 6B illustrates a needle with a thread attached thereto. The pancreas may be accessed by surgery or minimally invasively methods such as by laparoscopy. The distal end of the needle may be inserted into the pancreatic tumor. The needle then may traverse the pancreatic tumor as illustrated in FIG. 6C and then may exit the tumor. The needle may then be pulled distally until it is removed from the pancreatic tumor such that the thread is pulled into the location previously occupied by the needle. Finally, excess thread is cut from the needle which leaves the thread implanted in the pancreatic tumor. The process may be repeated any number of times to provide, as illustrated in FIG. 6D, a pancreatic tumor which has been implanted with a number of threads. In some embodiments, the thread includes an anti-cancer agent.

In some embodiments, a method for treating a varicose vein in subject in need thereof is provided. The thread may be attached to a needle as illustrated, for example, in FIGS. 1, 2A and 2B. The distal end of the needle may be inserted into the varicose vein of the subject. The needle then may traverse the varicose vein and then may exit the vein. The needle may then be pulled distally until it is removed from the varicose vein of the subject such that the thread is pulled into the location previously occupied by the needle. Finally, excess thread is cut from the needle which leaves the thread implanted in the varicose vein of the subject. In some embodiments, the needle is a flexible. In other embodiments, the thread coils when hydrated, more readily occluding the vessel.

Figure 7A:
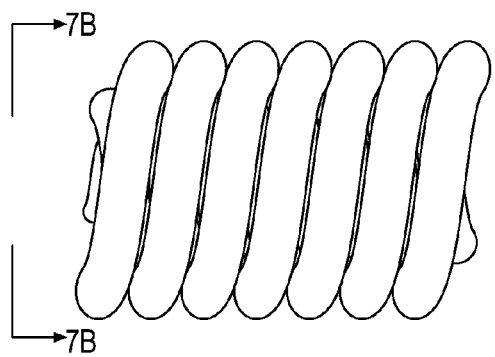
FIG. 7A illustrates multiple layers of concentric coils of thread, shaped to represent a human nipple.
Figure 7B:
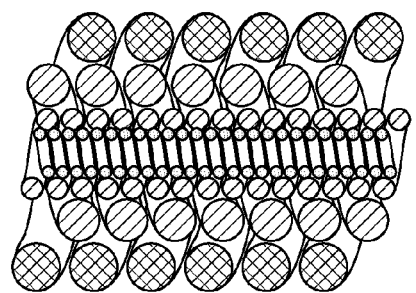
FIG. 7B illustrates the implant of FIG. 7A in cross-section.
Figure 7C:
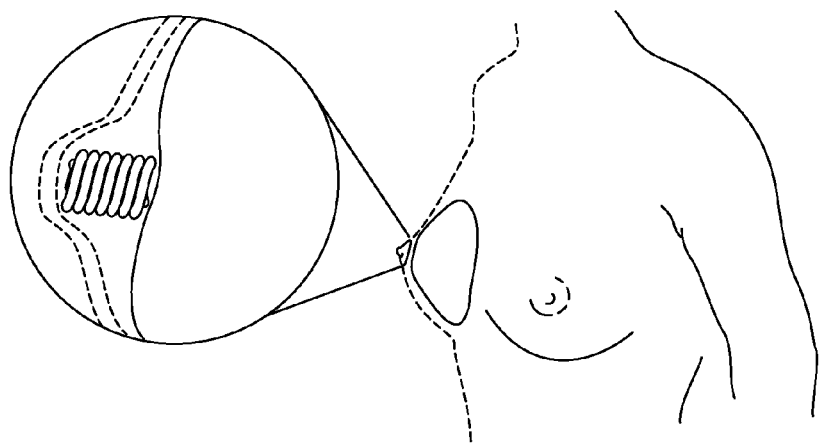
FIG. 7C illustrates how an implant of coiled thread would be used for nipple reconstruction.

In some embodiments, a method for nipple reconstruction is provided where a three-dimensional, cylindrical implant comprised of cross linked threads is implanted underneath the skin. The implant may include therapeutic agents, for example chrondrocyte adhesion compounds. FIG. 7A illustrates an implant of multiple layers of concentric coils of threads shaped to represent a nipple while FIG. 7B shows a cross-section of the implant of FIG. 7A. FIG. 7C illustrates how the implant of FIG. 7A could be used for nipple reconstruction.

Figure 8:
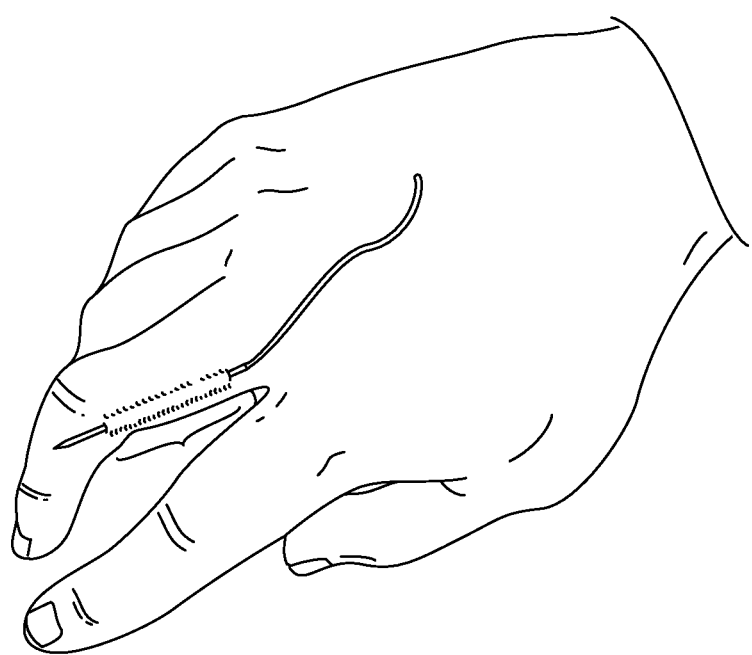
FIG. 8 illustrates how a needle and thread could be used to place a thread in a specific, linear location to promote nerve or vessel regrowth in a specific line.

In some embodiments, methods for nerve or vessel regrowth are provided. As illustrated in FIG. 8, a needle can be used to place a thread in a specific line which could promote nerve or vessel regeneration.

EXAMPLES

The present invention is further defined by reference to the following examples. It will be apparent to those skilled in the art that many modifications, both to materials and methods, may be practiced without departing from the scope of the current invention.

Example 1

Synthesis of a Cross Linked Thread

A cross linked thread of a diameter between 0.004 in and 0.006 in was made by forming a gel with a concentration of 5% hyaluronic acid and 0.4% BDDE, by weight with the remainder comprised of water. A tapered tip nozzle with an inner diameter of 0.02 in, a syringe pressure of 20 psi and a linear translation speed commensurate with the speed of gel ejection from the syringe was used to extrude the gel into a thread form. However, numerous combinations of extrusion parameters that can make a thread of the desired thickness exist. The thread was dried and then rinsed with water which hydrated the thread, which was then stretched during drying. Over the course of multiple rinsing and drying cycles the overall length of the thread was increased by between about 25% and about 100%. The thread made as described above will fail at a tensile force of about between about 0.25 kg and about 1.50 kg and will swell in diameter by about 25% and about 100% when hydrated. It may persist as a thread in vivo between 1 and 9 months.

Example 2

Treatment of Wrinkles of a Cadaver with Hyaluronic Acid Threads

Hypodermic needles (22 to 25 Ga) were affixed with single or double strands of hyaluronic acid threads, ranging from thicknesses of 0.004 in to 0.008 in. Both non-crosslinked threads and threads crosslinked using BDDE were used. The needles were able to traverse wrinkles in a cadaveric head of a 50 y/o woman such as the naso-labial fold, peri-orals, peri-orbitals, frontalis (forehead), and glabellar. The needle was able to pull the thread through the skin such that the thread was located where the needle was previously inserted.

Example 3

Placement of Hyaluronic Acid Threads in Dogs

Acute and chronic canine studies were performed. Hypodermic needles (22 to 25 Ga) were affixed with single or double strands of hyaluronic acid threads, ranging from thicknesses of 0.004 in to 0.008 in. Both non-crosslinked threads and threads cross linked using BDDE were used. In all cases, the needle was able to pull the attached thread or threads into the dermis. Within minutes most threads produced a visible impact on the skin surface of the animals in the form of a linear bump.

Example 4

Comparison of Tensile Strength of Different Hyaluronic Acid Threads

The tensile strength of an autocrosslinked thread of hyaluronic acid was compared to a thread cross linked using the method of Example 1. A thread of non-crosslinked hyaluronic acid was repeatedly frozen and thawed, replicating a method of autocrosslinking hyaluronic acid (Ref. U.S. Pat. No. 6,387,413). All such samples had less tensile force at failure than a thread made using the same extrusion parameters and cross-linked using BDDE as described above.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All references and publications cited herein are incorporated by reference in their entirety.

What is claimed is:

1. A dried thread comprised of (i) cross linked hyaluronic acid or a salt(s) thereof, wherein the cross linked hyaluronic acid has been cross linked with butanediol diglycidyl ether (BDDE), and (ii) non-cross linked hyaluronic acid or a salt(s) thereof.

2. The thread of claim 1, further comprising a needle, and wherein the dried thread includes an end attached to the needle.

3. The thread of claim 1, wherein the dried thread has a diameter of between about 0.0001 and about 0.020 in.

4. The thread of claim 1, wherein the degree of cross linking between the hyaluronic acid or salt thereof and the cross linking agent is between about 0.01% and about 20%.

5. The thread of claim 1, wherein the dried thread has sufficient mechanical strength for dermal implantation.

6. The thread of claim 1, wherein the dried thread will fail at a tensile force of between about 0.1 lbs and about 5 lbs.

7. The thread of claim 1, wherein the dried thread has an ultimate tensile strength of between about 1 kpsi and about 125 kpsi.

8. The thread of claim 1 wherein the thread is swellable when hydrated.

9. A dermal filler comprising the thread of claim 1.

10. A method of treating a wrinkle comprising implanting in a subject in need thereof the thread of claim 1 beneath the wrinkle.

11. The method of claim 10, wherein the method comprises attaching the thread to a needle; inserting the distal end of the needle through the skin surface of the subject into the dermis of the subject adjacent to the wrinkle; traversing the dermis of the subject under the wrinkle with the needle; forcing the needle through the skin surface of the subject; and cutting the thread from the needle at the skin surface of the subject.

12. A dried thread comprised of crosslinked hyaluronic acid or a salt(s) thereof, wherein the cross linked hyaluronic acid has been cross linked with butanediol diglycidyl ether (BDDE).

13. A dried thread comprised of crosslinked hyaluronic acid or a salt(s) thereof, wherein the crosslinked hyaluronic acid consists essentially of hyaluronic acid that has been crosslinked with butanediol diglycidyl ether (BDDE).

14. A dried thread comprised of cross linked hyaluronic acid or a salt(s) thereof, wherein the cross linked hyaluronic acid has been cross linked with butanediol diglycidyl ether (BDDE);
wherein the thread is a single strand thread; and
wherein the thread is capable of being hydrated, and when hydrated will swell in diameter by about 25% and about 100%.

15. The thread of claim 14 wherein the degree of crosslinking is between about 0.1% and about 10%.

16. The thread of claim 15 wherein the degree of crosslinking is between about 1% and about 8%.

17. The thread of claim 14 wherein the thread persists in vivo between 1 and 9 months after implantation in the dermis.

* * * * *

UNITED STATES PATENT AND TRADEMARK OFFICE
CERTIFICATE OF CORRECTION

PATENT NO. : 9,228,027 B2
APPLICATION NO. : 13/060919
DATED : January 5, 2016
INVENTOR(S) : Geoffrey C. Gurtner et al.

Page 1 of 2

It is certified that error appears in the above-identified patent and that said Letters Patent is hereby corrected as shown below:

Title Page

On the Page 5, in column 1, item (56) under "Other Publications", line 54, delete "L," and insert -- I., --, therefor.

On the Page 5, in column 2, item (56) under "Other Publications", line 8, delete "Breats" and insert -- Breast --, therefor.

On the Page 5, in column 2, item (56) under "Other Publications", line 20, delete "Sponse:" and insert -- Sponge: --, therefor.

On the Page 6, in column 1, item (56) under "Other Publications", line 8, delete "An Theum" and insert -- Ann Rheum --, therefor.

On the Page 6, in column 1, item (56) under "Other Publications", line 14, delete "Iriitants:" and insert -- Irritants: --, therefor.

On the Page 6, in column 1, item (56) under "Other Publications", line 30, delete "Institue" and insert -- Institute --, therefor.

On the Page 6, in column 1, item (56) under "Other Publications", line 44, delete "ACS),"" and insert -- *ACS)," --, therefor.

On the Page 6, in column 1, item (56) under "Other Publications", line 47, delete "Compunds" and insert -- Compounds --, therefor.

On the Page 6, in column 1, item (56) under "Other Publications", line 63, delete "Plastric" and insert -- Plastic --, therefor.

On the Page 6, in column 1, item (56) under "Other Publications", line 66, delete "(Supp)1):7" and insert -- (Suppl1):7 --, therefor.

On the Page 6, in column 2, item (56) under "Other Publications", line 15, delete "1-ethy1" and insert -- 1-ethyl --, therefor.

Signed and Sealed this
Nineteenth Day of April, 2016

Michelle K. Lee
*Director of the United States Patent and Trademark Office*

CERTIFICATE OF CORRECTION (continued)

Title Page

On the Page 6, in column 2, item (56) under "Other Publications", line 54, delete "etal" and insert -- et al., --, therefor.

On the Page 6, in column 2, item (56) under "Other Publications", line 55, delete "Crosslinkedwith" and insert -- Crosslinked with --, therefor.

On the Page 6, in column 2, item (56) under "Other Publications", line 55, delete "Glyol" and insert -- Glycol --, therefor.

On the Page 6, in column 2, item (56) under "Other Publications", line 56, delete "Tetracrylates";" and insert -- Tetraacrylates"; --, therefor.

On the Page 6, in column 2, item (56) under "Other Publications", line 62, delete "Hyalruonic" and insert -- Hyaluronic --, therefor.

On the Page 6, in column 2, item (56) under "Other Publications", line 66, delete "Viscoelstic" and insert -- Viscoelastic --, therefor.

Specification

In column 1, line 28, delete "acetylglucoamine" and insert -- acetylglucosamine --, therefor.

In column 1, line 32, delete "hylauronic" and insert -- hyaluronic --, therefor.

In column 2, line 41, delete "opthamology," and insert -- ophthalmology, --, therefor.

In column 4, line 28, delete "galactunoric" and insert -- galacturonic --, therefor.

In column 4, line 37, delete "fermentation" and insert -- fermentation. --, therefor.

In column 5, lines 13-14, delete "ripivacaine," and insert -- ropivacaine, --, therefor.

In column 12, line 37, delete "chrondrocyte" and insert -- chondrocyte --, therefor.